(12) United States Patent
Hanson et al.

(10) Patent No.: US 10,342,609 B2
(45) Date of Patent: Jul. 9, 2019

(54) MEDICAL DEVICES FOR RENAL NERVE ABLATION

(71) Applicant: Boston Scientific Scimed, Inc., Maple Grove, MN (US)

(72) Inventors: Cass A. Hanson, St. Paul, MN (US); Derek C. Sutermeister, Ham Lake, MN (US); Daniel T. Quillin, Eden Prairie, MN (US); Hong Cao, Maple Grove, MN (US); Jeffrey S. Lindquist, Maple Grove, MN (US); Adam J. Royer, Brooklyn Park, MN (US); Timothy A. Ostroot, Cokato, MN (US); James M. Anderson, Corcoran, MN (US); Jan Weber, Maastricht (NL); Robert N. Squire, Maple Grove, MN (US); Martin R. Willard, Burnsville, MN (US); Patrick A. Haverkost, Brooklyn Center, MN (US); Daniel J. Horn, Shoreview, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1388 days.

(21) Appl. No.: 14/336,778

(22) Filed: Jul. 21, 2014

(65) Prior Publication Data

US 2015/0025532 A1  Jan. 22, 2015

Related U.S. Application Data

(60) Provisional application No. 61/857,050, filed on Jul. 22, 2013, provisional application No. 61/907,978, filed on Nov. 22, 2013.

(51) Int. Cl.
*A61B 18/18* (2006.01)
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00148* (2013.01);
(Continued)

(58) Field of Classification Search
CPC ...... A61B 2018/00434; A61B 18/1492; A61B 2018/00511; A61B 2018/00404; A61B 2018/00577
See application file for complete search history.

(56) References Cited

U.S. PATENT DOCUMENTS 164,184 A   6/1875  Kiddee
852,787 A   5/1907  Hoerner
(Continued)

FOREIGN PATENT DOCUMENTS

DE   10038737 A1   2/2002
EP    1053720 A1  11/2000
(Continued)

OTHER PUBLICATIONS

US 8,398,630 B2, 03/2013, Demarais et al. (withdrawn)
(Continued)

*Primary Examiner* — Michael J D Abreu

(57) ABSTRACT

Medical devices and methods for making and using the same are disclosed. An example medical device may include a medical device for tissue ablation. The medical device may include an elongated shaft having a distal region. An inflatable balloon may be mounted to the distal region. The inflatable balloon may include a body region, a proximal waist, a distal waist, a proximal cone region, and a distal cone region. A skirt may be attached to the inflatable balloon and may extend proximally from the body region. An electrode assembly may be applied directly to an outer surface of the body region of the inflatable balloon. The electrode assembly may include a first conductive member
(Continued)

applied directly to the outer surface of the body region of the inflatable balloon and extending proximally therefrom along an outer surface of the skirt.

11 Claims, 30 Drawing Sheets

(52) U.S. Cl.
CPC .............. *A61B 2018/00404* (2013.01); *A61B 2018/00434* (2013.01); *A61B 2018/00511* (2013.01); *A61B 2018/00577* (2013.01); *A61B 2018/00791* (2013.01); *A61B 2018/00815* (2013.01); *A61B 2018/00821* (2013.01); *Y10T 156/10* (2015.01)

(56) References Cited

U.S. PATENT DOCUMENTS

| | | |
|---|---|---|
| 921,973 A | 5/1909 | Gillett et al. |
| 976,733 A | 11/1910 | Gilliland |
| 1,167,014 A | 1/1916 | O'Brien |
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,531,943 A | 7/1985 | Van Tassel et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,890,623 A | 1/1990 | Cook et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,290,306 A | 3/1994 | Trotta et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,512,051 A | 4/1996 | Wang et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |

(56) References Cited

U.S. PATENT DOCUMENTS

| | | |
|---|---|---|
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,613,979 A | 3/1997 | Trotta et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,687,737 A | 11/1997 | Branham et al. |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,807,306 A | 9/1998 | Shapland et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh |
| 6,030,611 A | 2/2000 | Gorecki et al. |
| 6,032,675 A | 3/2000 | Rubinsky et al. |
| 6,033,397 A | 3/2000 | Laufer et al. |

(56) References Cited

U.S. PATENT DOCUMENTS

| | | | |
|---|---|---|---|
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,091,995 A | 7/2000 | Ingle et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,110,192 A | 8/2000 | Ravenscroft et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A * | 9/2000 | Tu .................. A61B 18/14 606/41 |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |

(56) References Cited

U.S. PATENT DOCUMENTS

| | | |
|---|---|---|
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 * | 12/2002 | Maguire ............ A61B 18/1492 606/41 |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung |
| 6,602,246 B1 | 8/2003 | Joye et al. |
| 6,605,056 B2 | 8/2003 | Eidenschink et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |

(56) References Cited

U.S. PATENT DOCUMENTS

| | | |
|---|---|---|
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,923,808 B2 | 8/2005 | Taimisto |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |

(56) References Cited

U.S. PATENT DOCUMENTS

| | | |
|---|---|---|
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,480 B2 | 1/2008 | Eidenschink et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,686,841 B2 | 3/2010 | Eidenschink et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |

(56) References Cited

U.S. PATENT DOCUMENTS

| | | |
|---|---|---|
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,043,673 B2 | 10/2011 | Lee et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarais et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,168,275 B2 | 5/2012 | Lee et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |

(56) References Cited

U.S. PATENT DOCUMENTS

| | | |
|---|---|---|
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0050635 A1 | 3/2003 | Truckai et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2003/0229340 A1 | 12/2003 | Sherry et al. |
| 2003/0233099 A1 | 12/2003 | Danaek et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0096647 A1 | 5/2005 | Steinke et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2005/0273149 A1 | 12/2005 | Tran et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0085054 A1 | 4/2006 | Zikorus et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0182873 A1 | 8/2006 | Klisch et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0067883 A1 | 3/2007 | Sretavan |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0203549 A1 | 8/2007 | Demarais et al. |

(56) References Cited

U.S. PATENT DOCUMENTS

| | | |
|---|---|---|
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0125268 A1 | 5/2010 | Gustus et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |

(56) References Cited

U.S. PATENT DOCUMENTS

| | | |
|---|---|---|
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2012/0310233 A1 | 12/2012 | Dimmer et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066316 A1 | 3/2013 | Steinke et al. |
| 2013/0085489 A1 | 4/2013 | Fain et al. |
| 2013/0085493 A1 | 4/2013 | Bloom et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |
| 2014/0074083 A1 | 3/2014 | Horn et al. |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |

(56) References Cited

FOREIGN PATENT DOCUMENTS

| | | |
|---|---|---|
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| JP | 2012086492 | 5/2012 |
| WO | 9531142 A1 | 11/1995 |
| WO | 9858588 A1 | 12/1998 |
| WO | 9900060 A1 | 1/1999 |
| WO | 9935986 | 7/1999 |
| WO | 0047118 A1 | 8/2000 |
| WO | 0066021 | 11/2000 |
| WO | 0195820 | 12/2001 |
| WO | 03026525 A1 | 4/2003 |
| WO | 2004100813 A2 | 11/2004 |
| WO | 2004110258 A2 | 12/2004 |
| WO | 2005041810 | 5/2005 |
| WO | 2006105121 A2 | 10/2006 |
| WO | 2008014465 A2 | 1/2008 |
| WO | 2009001327 A2 | 12/2008 |
| WO | 2009121017 A1 | 10/2009 |
| WO | 2010067360 A2 | 6/2010 |
| WO | 2010102310 A2 | 9/2010 |
| WO | 2010132703 | 11/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2013049601 A2 | 4/2013 |

OTHER PUBLICATIONS

Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Products—Functional Measurement," Volcano Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.

Fram et al., "Feasibility of Radiofrequency Powered, Thermal Balloon Ablation of Atrioventricular Bypass Tracts via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-49, Nov. 6, 1997.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Popma et al., "Percutaneous Coronary and Valvular Intervention," Braunwald's Heart Disease: A Textbook of Cardiovascular Medicine, 7th edition, p. 1364-1405, 2005.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.

(56) References Cited

OTHER PUBLICATIONS

Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
"Optical Coherence Tomography: Advantages of OCT," LightLab Imaging Technology, printed Sep. 3, 2003.
"Optical Coherence Tomography: Image Gallery Cardiovascular Procedures," LightLab Imaging Technology, printed Sep. 3, 2003.
"Optical Coherence Tomography: What is OCT?," LightLab Imaging Technology, printed Sep. 3, 2003.
"Optical Coherence Tomography: Why Use OCT?," LightLab Imaging Technology, printed Sep. 3, 2003.
Pieper et al. "Design and implementation of a new computerized system for intraoperative cardiac mapping", J. Appl. Physiol. 71(4): 1529-1539, 1991.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18, 2004.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572, Dec. 2004.
Baun, "Interaction with Soft Tissue," Principles of General & Vascular Sonography, Chapter 2, pp. 23-24, Before Mar. 2012.
Blue Cross Blue Shield Medical Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhou et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.

\* cited by examiner

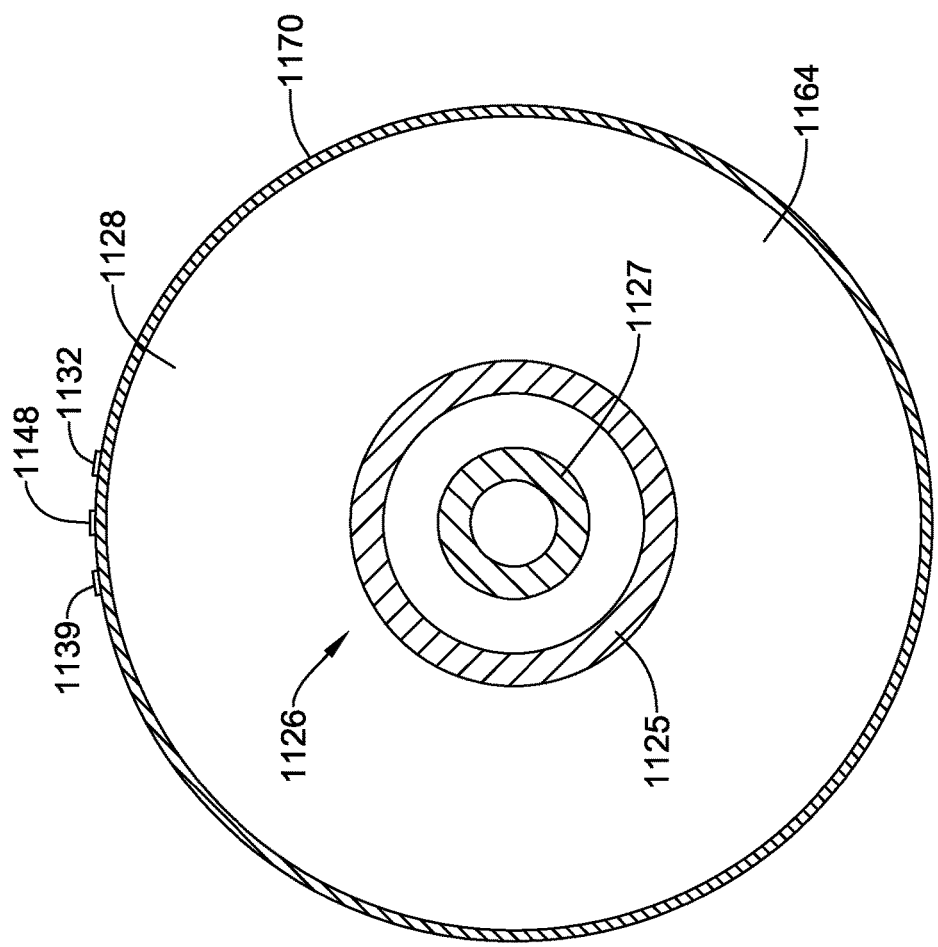

MEDICAL DEVICES FOR RENAL NERVE ABLATION

CROSS-REFERENCE TO RELATED APPLICATIONS

This application claims priority under 35 U.S.C. § 119 to U.S. Provisional Application Ser. No. 61/857,050, filed Jul. 22, 2013 and U.S. Provisional Application Ser. No. 61/907,978, the entire disclosures of which are incorporated herein by reference.

TECHNICAL FIELD

The present disclosure pertains to medical devices, and methods for manufacturing medical devices. More particularly, the present disclosure pertains to medical devices for renal nerve ablation.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include a medical device for renal nerve ablation. The medical device may include an elongated shaft having a distal region. An expandable member may be coupled to the distal region. One or more active electrodes may be coupled to the expandable member. A common ground electrode may be coupled to the expandable member. The common ground electrode may be capable of being a ground pathway for all of the one or more active electrodes.

Another example medical device for renal nerve ablation may include an elongated shaft having a distal region. An expandable balloon may be coupled to the distal region. A plurality of active electrodes may be coupled to the balloon. A common ground electrode may be coupled to the balloon. The common ground electrode may be capable of being a ground pathway for all of the active electrodes.

Methods for ablating renal nerves are also disclosed. An example method may include providing a medical device. The medical device may include an elongated shaft having a distal region. An expandable member may be coupled to the distal region. One or more active electrodes may be coupled to the expandable member. A common ground electrode may be coupled to the expandable member. The common ground electrode may be capable of being a ground pathway for all of the one or more active electrodes. The method may also include advancing the medical device through a blood vessel to a position within a renal artery, expanding the expandable member, and activating at least some of the one or more active electrodes.

Another example medical device may include a catheter shaft having a distal region. A balloon may be coupled to the distal region. The balloon may include a first layer of conductive material and a second layer of non-conductive material. One or more conductive regions may be defined along the balloon at regions that are free of the second layer. A conductive fluid may be disposed within the balloon. An active electrode may be disposed along an outer surface of the balloon. A return electrode may be disposed within the balloon. The first layer may be an inner layer of the balloon and the second layer may be an outer layer of the balloon.

An example method for manufacturing a medical device may include providing a balloon having an outer surface, forming a plurality of grooves in the outer surface of the balloon, disposing an electrode in each of the grooves, and disposing a common return electrode along the outer surface, the common return being positioned adjacent to each of the electrodes.

Another example medical device for renal nerve ablation may include a catheter shaft. An expandable balloon may be coupled to the catheter shaft. The balloon may have a length, and inner layer, and an outer layer. The outer layer may have a plurality of conductive regions formed therein that extend along the length balloon. The outer layer may also have a plurality of non-conductive regions formed therein and disposed adjacent to the conductive region. An electrode may be coupled to the conductive region.

Another example medical device may include a medical device for renal nerve ablation. The medical device may include an elongated shaft having a distal region. An expandable member may be coupled to the distal region. One or more active electrodes may be coupled to the expandable member. A common ground electrode may be coupled to the expandable member. The common ground electrode may include a conductive member and a plurality of ground pads coupled to the conductive member. The common ground electrode may be capable of being a ground pathway for all of the one or more active electrodes.

Another example medical device may include a medical device for tissue ablation. The medical device may include an elongated shaft having a distal region. An inflatable balloon may be mounted to the distal region. The inflatable balloon may include a body region, a proximal waist secured to the elongated shaft, a distal waist secured to the elongated shaft, a proximal cone region intermediate the proximal waist and the body region, and a distal cone region intermediate the body region and the distal waist. A skirt may be attached to the inflatable balloon and extend proximally from the body region. An electrode assembly may be applied directly to an outer surface of the body region of the inflatable balloon. The electrode assembly may include a first conductive member applied directly to the outer surface of the body region of the inflatable balloon and extending proximally therefrom along an outer surface of the skirt.

Another example medical device may include a medical device for tissue ablation. The medical device may include an elongated shaft having a distal region. An inflatable balloon may be mounted to the distal region. The inflatable balloon may include a body region, a proximal waist secured to the elongated shaft, a distal waist secured to the elongated shaft, a proximal cone region intermediate the proximal waist and the body region, and a distal cone region intermediate the body region and the distal waist. A skirt may have a distal portion attached to an outer surface of the body region of the inflatable balloon and a proximal portion extending proximal of the body region of the inflatable balloon. An electrode assembly may be disposed on the body region of the inflatable balloon. The electrode assembly may include an active electrode applied directly to the outer surface of the body region of the inflatable balloon. The electrode assembly may include a return electrode applied directly to the outer surface of the body region of the inflatable balloon. The electrode assembly may also include a first conductive member extending proximally from the active electrode. The first conductive member may be applied directly to the outer surface of the body region of the inflatable balloon and applied directly to an outer surface of the skirt. The electrode assembly may also include a second conductive member extending proximally from the return electrode. The second conductive member may be applied directly to the outer surface of the body region of the inflatable balloon and applied directly to the outer surface of the skirt.

Another example method may include a method of forming a medical device for tissue ablation. The method may include securing a skirt to an inflatable balloon mounted on a catheter shaft. The skirt may extend proximal of a body region of the inflatable balloon. An electrode may be applied directly to an outer surface of the body region of the inflatable balloon. A conductive member may be applied directly to the outer surface of the body region of the inflatable balloon and directly to an outer surface of the skirt. The conductive member may extend proximally from the electrode to a proximal end region of the skirt.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 17A is a cross-sectional view taken along line 17A-17A in FIG. 17;

Figure 1:
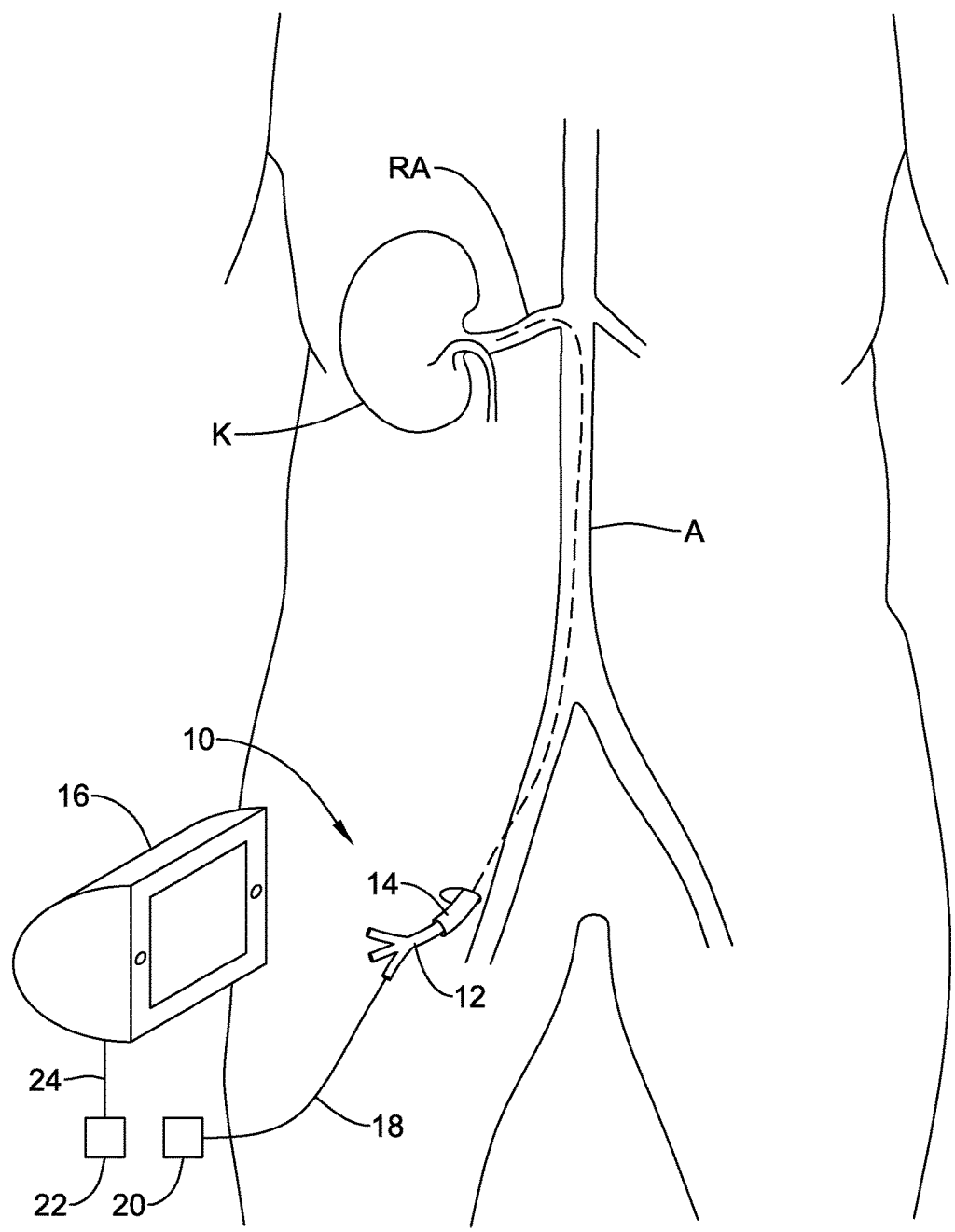
FIG. 1 is a schematic view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Certain treatments are aimed at the temporary or permanent interruption or modification of select nerve function. One example treatment is renal nerve ablation, which is sometimes used to treat conditions such as or related to hypertension, congestive heart failure, diabetes, or other conditions impacted by high blood pressure or salt retention. The kidneys produce a sympathetic response, which may increase the undesired retention of water and/or sodium. The result of the sympathetic response, for example, may be an increase in blood pressure. Ablating some of the nerves running to the kidneys (e.g., disposed adjacent to or otherwise along the renal arteries) may reduce or eliminate this sympathetic response, which may provide a corresponding reduction in the associated undesired symptoms (e.g., a reduction in blood pressure).

While the devices and methods described herein are discussed relative to renal nerve ablation and/or modulation, it is contemplated that the devices and methods may be used in other treatment locations and/or applications where nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, cardiac ablation, pulmonary vein isolation, pulmonary vein ablation, tumor ablation, benign prostatic hyperplasia therapy, nerve excitation or blocking or ablation, modulation of muscle activity, hyperthermia or other warming of tissues, etc.

FIG. 1 is a schematic view of an example renal nerve modulation system 10. System 10 may include a renal nerve ablation medical device 12. Renal nerve ablation device 12 may be used to ablate nerves (e.g., renal nerves) disposed adjacent to the kidney K (e.g., renal nerves disposed about a renal artery RA). In use, renal nerve ablation device 12 may be advanced through a blood vessel such as the aorta A to a position within the renal artery RA. This may include advancing renal nerve ablation device 12 through a guide sheath or catheter 14. When positioned as desired, renal nerve ablation device 12 may be activated to energize one or more electrodes (not shown). This may include coupling renal nerve ablation device 12 to a generator 16 so as to supply the desired energy to the electrodes. For example, renal nerve ablation device 12 may include a wire or conductive member 18 with a connector 20 that can be connected to a connector 22 on generator 16 and/or a wire 24 coupled to generator 16. In at least some embodiments, generator 16 may also be utilized to supply/receive the appropriate electrical energy and/or signal to one or more sensors disposed at or near a distal end of renal nerve modulation device 12. When suitably activated, the electrodes may be capable of ablating tissue (e.g., renal nerves) as described below and the sensors may be used to sense desired physical and/or biological parameters.

Figure 2:
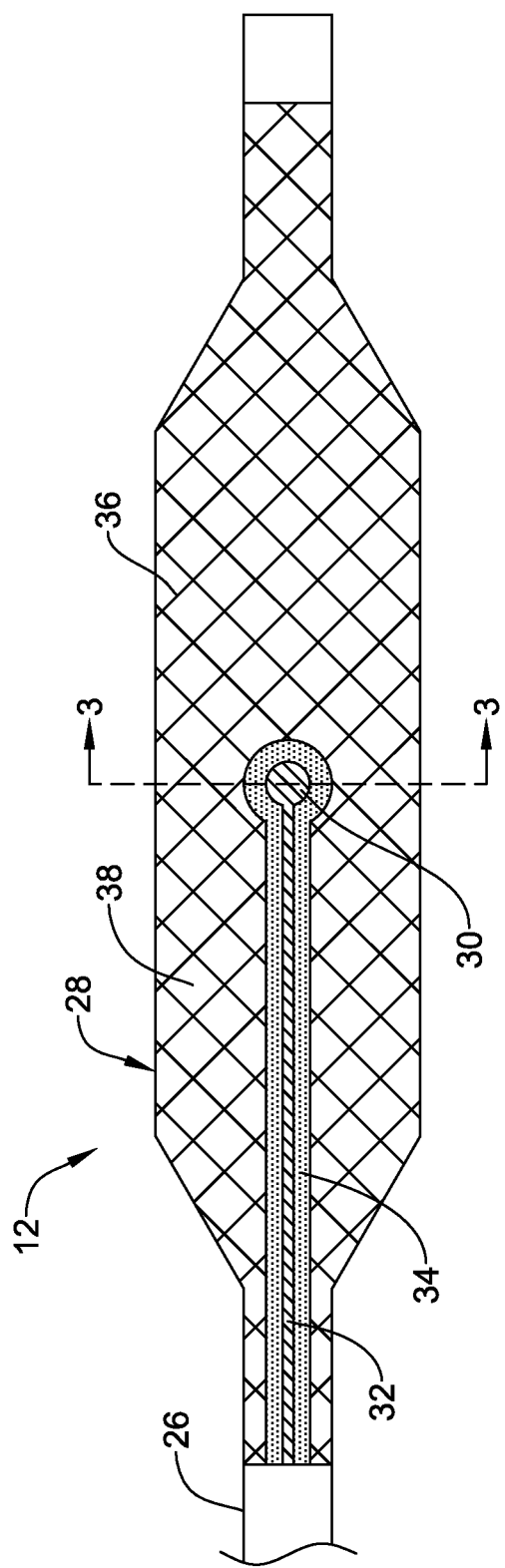
FIG. 2 is a side view of a portion of an example medical device.

FIG. 2 is a side view illustrating a portion of renal nerve ablation device 12. Here it can be seen that device 12 may include a tubular member or catheter shaft 26. An expandable member 28 may be coupled to catheter shaft 26. In at least some embodiments, expandable member 28 may be an expandable balloon. In other embodiments, expandable member 28 may include a basket, a plurality of struts, or the like.

An active electrode 30 may be coupled to expandable member 28. In at least some embodiments, active electrode 30 may be an ablation electrode that is capable of delivering ablation energy to a suitable target. For example, active electrode 30 may be capable of delivering ablation energy to tissue positioned adjacent to a blood vessel such as renal nerves positioned adjacent to a renal artery.

A conductive member 32 may be coupled to active electrode 30. Conductive member 32 may take the form of a conductive trace, a conductive wire, or the like. Conductive member 32 may be coupled to or be a region of conductive member 18 and, ultimately, may be coupled to generator 16. Thus, a suitable energy (e.g., RF energy) may be delivered to active electrode 30 via conductive member 32. A non-conductive or insulator layer 34 may be disposed adjacent to conductive member 32. Active electrode 30 may be disposed along non-conductive layer 34. Non-conductive layer 34 may insulate active electrode and/or conductive member 32 from other structures including conductive structures along expandable member 28 (e.g., which may include the common ground electrode 36). In other embodiments, active electrode 30 may be disposed along a flexible circuit (e.g., a "flex circuit"). Some example flex circuits that may be utilized for device 12 (and/or other devices disclosed herein) may include or otherwise be similar to flex circuits disclosed in U.S. patent application Ser. No. 13/760,846, the entire disclosure of which is herein incorporated by reference. For example, the flex circuit may include one or more polymeric layers (e.g., polyimide, polyethylene terephthalate (PET), polyethylene naphthalate (PEN)) with electrode (s) and conductive member(s) coupled thereto. In other embodiments, active electrode 30 may be disposed along a printed circuit.

Figure 3:
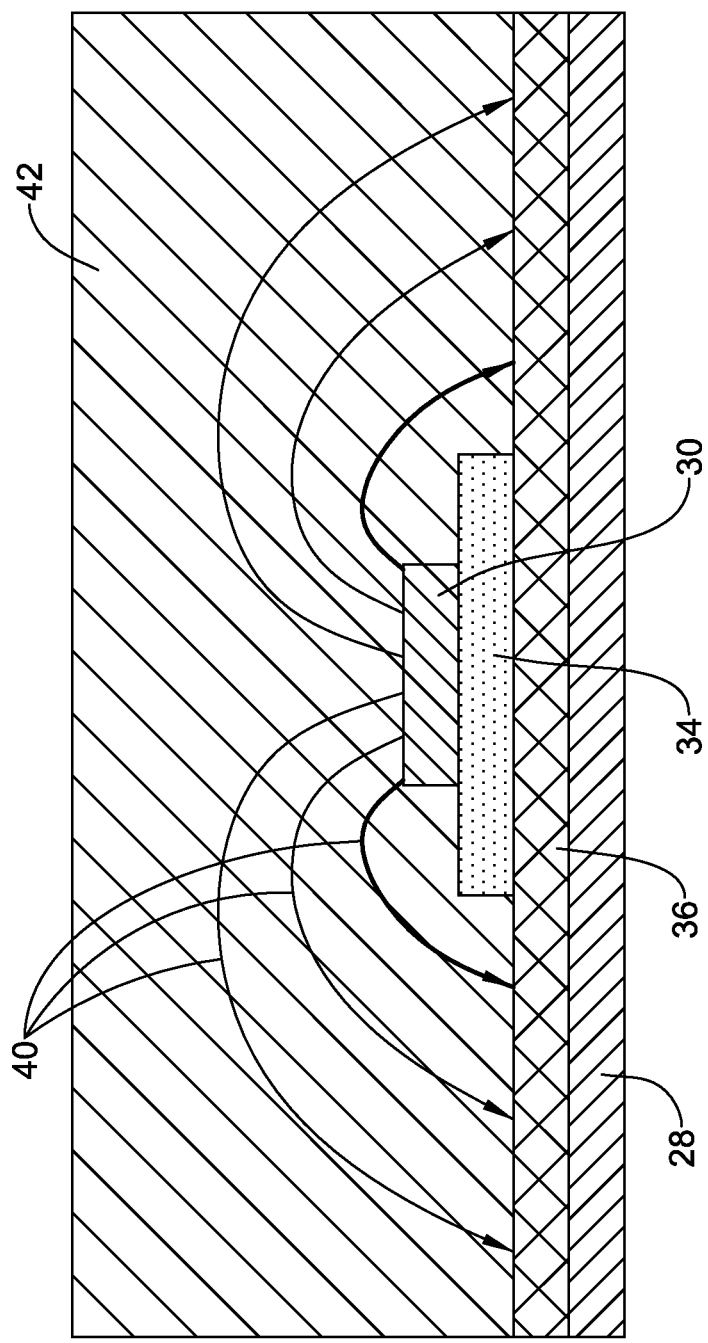
FIG. 3 is partial cross-sectional view taken through line 3-3 in FIG. 3.

A common return or ground electrode 36 may be disposed along an outer surface 38 of expandable member 28. Common ground electrode 36 may be capable of being a return electrical pathway for active electrode 30. Thus, energy may be delivered to active electrode 30 and common ground electrode 36 may be the return electrical pathway. For example, FIG. 3 illustrates that energy 40 may be delivered by active electrode 30 to a body tissue 42 (which may include renal nerves) and then back to common ground electrode 36. In some embodiments, there may be some electrical current dispersion from active electrode 30 to common ground electrode 36. Accordingly, the current density on or along common ground electrode 36 may be reduced and no lesions may be created at regions of body tissue 42 disposed along common ground electrode 36.

Figure 4:
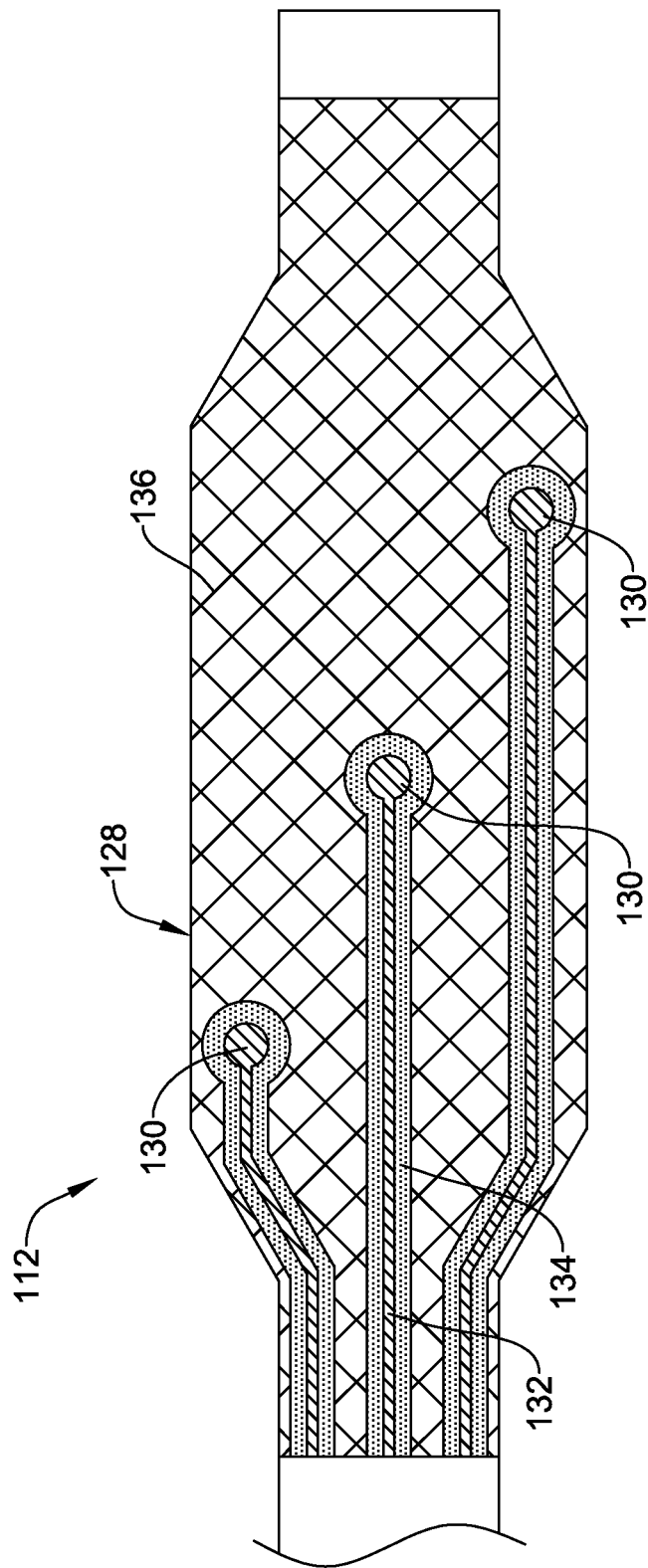
FIG. 4 is side view of another example medical device.

As the name suggests, common ground electrode 36 may be utilized as a common ground for more than one active electrode. For example, while only one active electrode 30 is shown in FIG. 2, device 12 may include a plurality of active electrodes 30 and common ground electrode 36 may be a common ground for at least some or, in at least some embodiments, all active electrodes 30. To further illustrate this feature, FIG. 4 illustrates device 112 having a plurality of active electrodes 130. Conductive member 132 may be coupled to electrodes 130. Non-conductive layer 134 may be disposed adjacent to conductive member 132 and/or electrodes 130. Common ground electrode 136 may be disposed along expandable member 128 and may be utilized as a common ground for at least some (e.g., all) active electrodes 130. Various embodiments of device 112 are contemplated that include any suitable number of active electrodes 130 including one, two, three, four, five, six, seven, eight, nine, ten, or more active electrodes 130.

Because common ground electrode 36/136 may be utilized at the return electrode for a plurality of active electrodes 30/130, active electrodes 30/130 need not have an individually dedicated bipolar return electrode paired with each active electrode 30/130. This may allow active electrodes 30/130 and/or the other structures associated therewith (e.g., the flex circuit, non-conductive layer 34/134, etc.) to be constructed with a smaller size or footprint, resulting in a lower profile, more flexible, more deliverable catheter. This smaller size or footprint may desirably impact the overall construction of device 12/112. For example, smaller active electrodes 30/130 may be more flexible, allow for more efficient balloon folding and refolding after treatment, before withdrawal through the sheath or guide. More efficient balloon folding can also provide fewer catch points or otherwise reduce the likelihood of edges of active electrodes 30/130 being lifted from the surface of expandable member 28 when proximally retracting device 12/112, reduce the profile of device 12/112, or the like. These are just examples.

In use, device 12/112 may be advanced through a blood vessel to a position adjacent to a target tissue (e.g., within a renal artery). In some embodiments, the target tissue may be one or more renal nerves disposed about the renal artery. When suitably positioned, expandable member 28 may be expanded. This may place active electrode 30/130 against the wall of the blood vessel. Active electrode 30/130 may be activated. Ablation energy may be transmitted from active electrode 30/130, through the target tissue (where renal nerves may be ablated, modulated, or otherwise impacted), and back through common ground electrode 36/136.

Figure 4A:
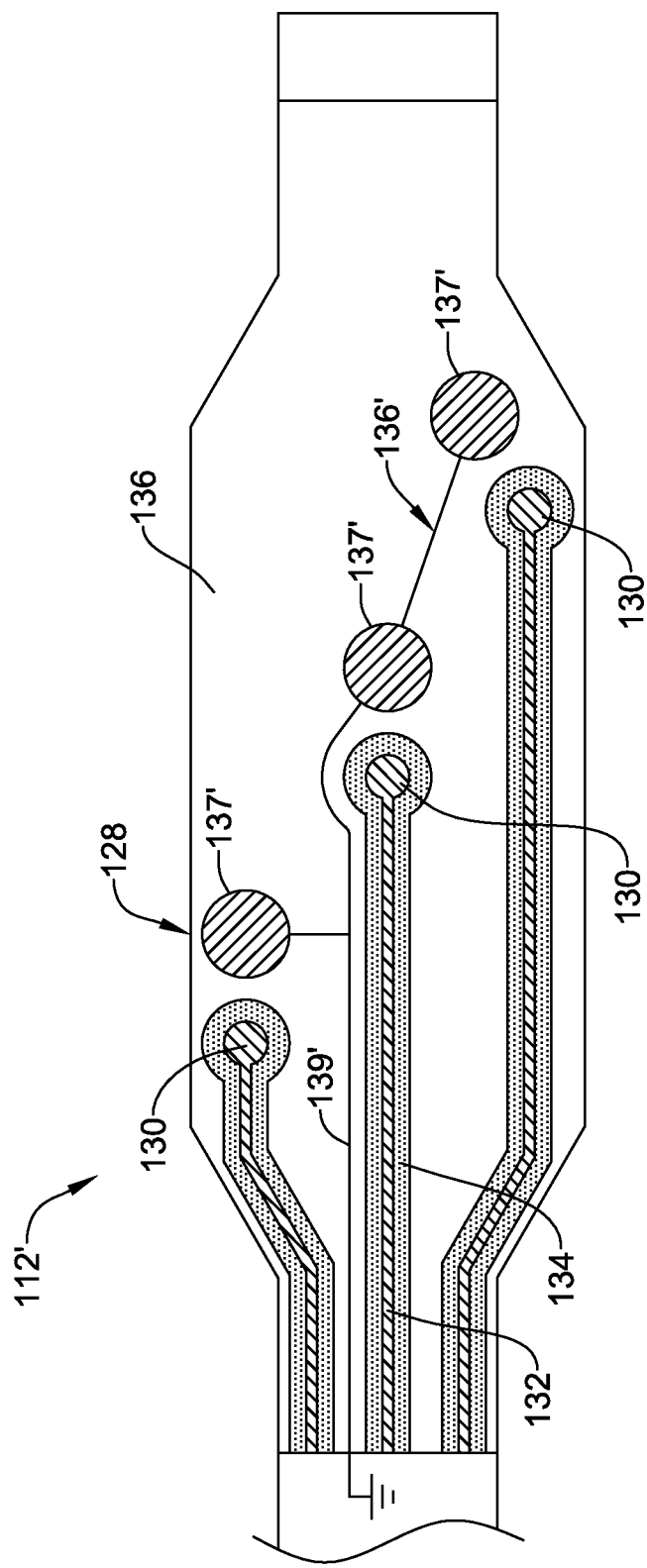
FIG. 4A is side view of another example medical device.

The form of common ground electrode 36/136 may also vary. For example, common ground electrode 36/136 may take the form of a grid or matrix of conductive material disposed along expandable member 28. Other embodiments are contemplated. FIG. 4A illustrates device 112' including common ground electrode 136' taking the form of a flexible circuit (e.g., a thin film flexible circuit). Common ground electrode 136' may include a conductive member 139' coupled to a plurality of ground pads 137'. Ground pads 137' may be disposed along expandable member 128 and generally positioned adjacent to active electrodes 130. In some embodiments, common ground electrode 136' includes one ground pad 137' for each active electrode 130. In other embodiments, fewer ground pads 137' may be included such that at least some of the ground pads 137' may act as a ground or return electrode for more than one active electrode 130.

Figure 5:
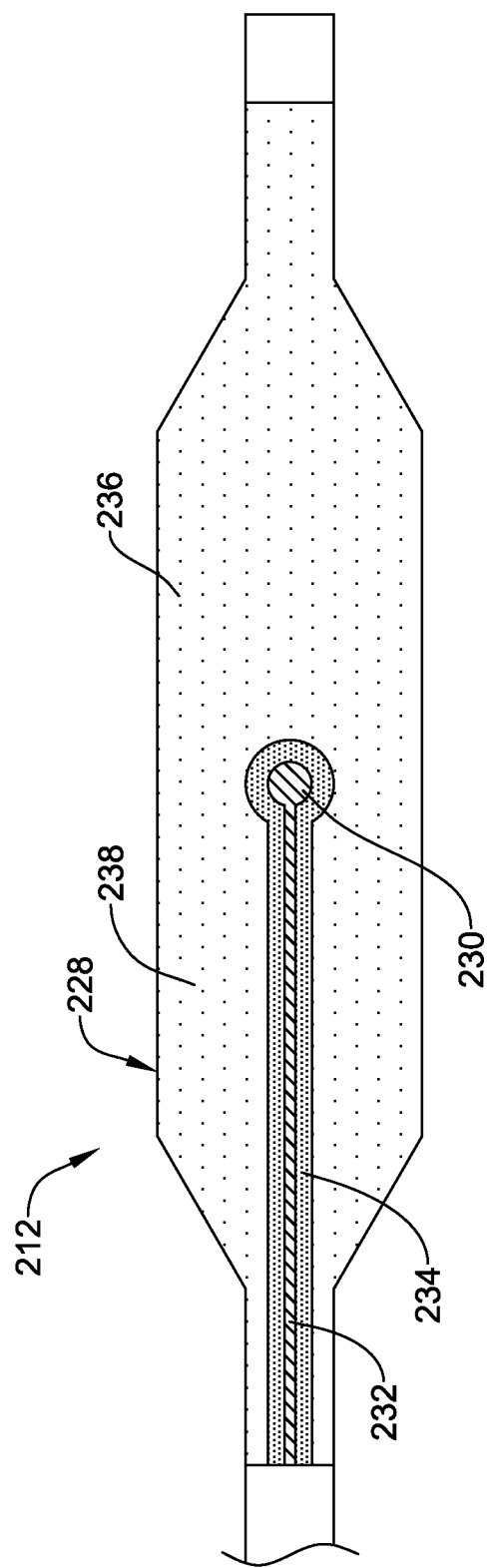
FIG. 5 is side view of another example medical device.

FIG. 5 illustrates device 212 having common ground electrode 236 taking the form of a conductive coating. Common ground electrode/coating 236 may be a return electrical pathway from one or more active electrodes 230. Active electrodes 230 may be coupled to conductive member 232. Non-conductive layer 234 may be disposed adjacent to conductive member 232 and/or active electrode(s) 230.

Coating 236 may be a conductive coating that is applied to a surface (e.g., outer surface 238) of expandable member 228. For example, coating 236 may be gold coating that may be sputter coated onto expandable member 228. Coating 236 may cover about 50% or more of the surface area of expandable member 228, or about 60% or more of the surface area of expandable member 228, or about 70% or more of the surface area of expandable member 228, or about 80% or more of the surface area of expandable member 228, or about 90% or more of the surface area of expandable member 228. These are just examples. Other coatings and coating application methods are contemplated and any suitable coatings can be utilized with any of the devices disclosed herein.

Figure 6:
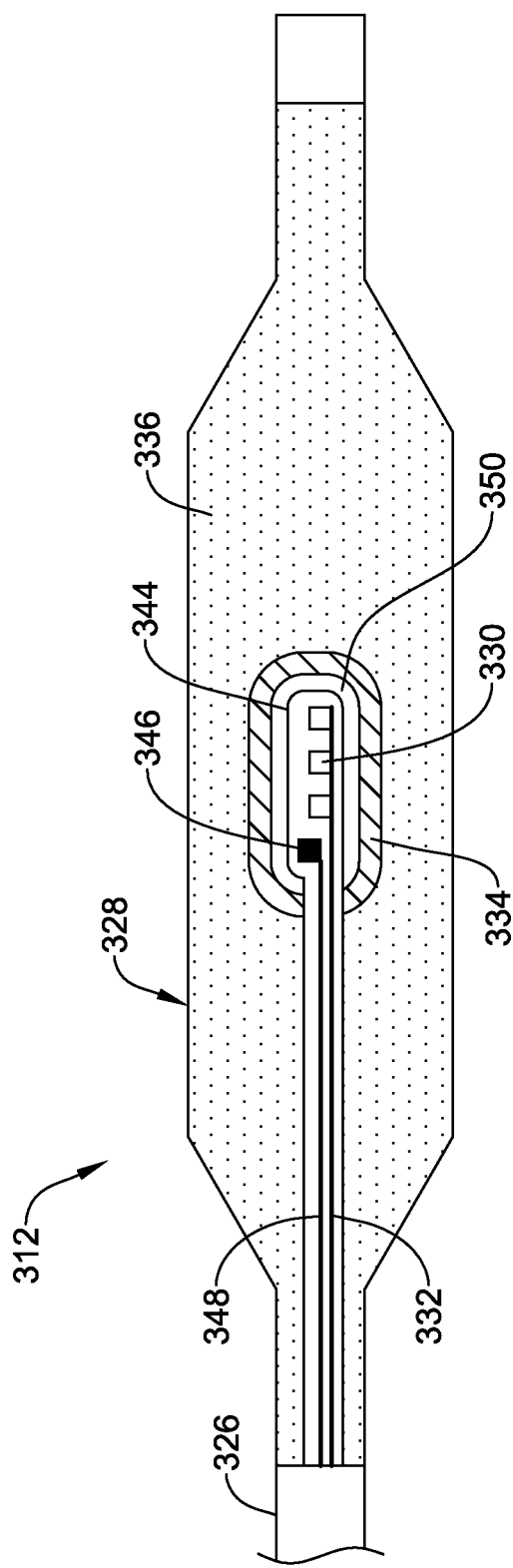
FIG. 6 is side view of another example medical device.

FIG. 6 illustrates another example device 312 that may be similar in form and function to other devices disclosed herein. Device 312 may include catheter shaft 326 having expandable member 328 coupled thereto. Expandable member 328 may include common ground electrode 336. For example, common ground electrode 336 may include a coating disposed along expandable member 328. In at least some embodiments, coating 336 may be a gold coating that may be, for example, sputter coated onto expandable member 328.

A flex circuit 344 may be disposed along expandable member 328. Flex circuit 344 may include one or more active electrodes 330. Conductive member 332 may be coupled to active electrodes 330. Optionally, a non-conductive layer 334 may be disposed about flex circuit 344. It can be appreciated that non-conductive layer 334 may not be needed when flex circuit 344 includes an insulating layer (e.g., is "self-insulated"). A temperature sensor 346 may also be coupled to flex circuit 344. Temperature sensor 346 may include a thermistor, thermocouple, or any other suitable temperature sensor. A conductive member 348 may be coupled to temperature sensor 346.

In at least some embodiments, flex circuit 344 may be disposed along a non-conductive region 350 of expandable member 328. For example, expandable member 328 may be masked and then coated with a conductive material to define common ground electrode 336. The mask may be removed, thereby defining non-conductive region 350, and flex circuit 344 may be disposed along non-conductive region 350. In other embodiments, flex circuit 344 may be disposed directly onto coating 336.

Figure 7:
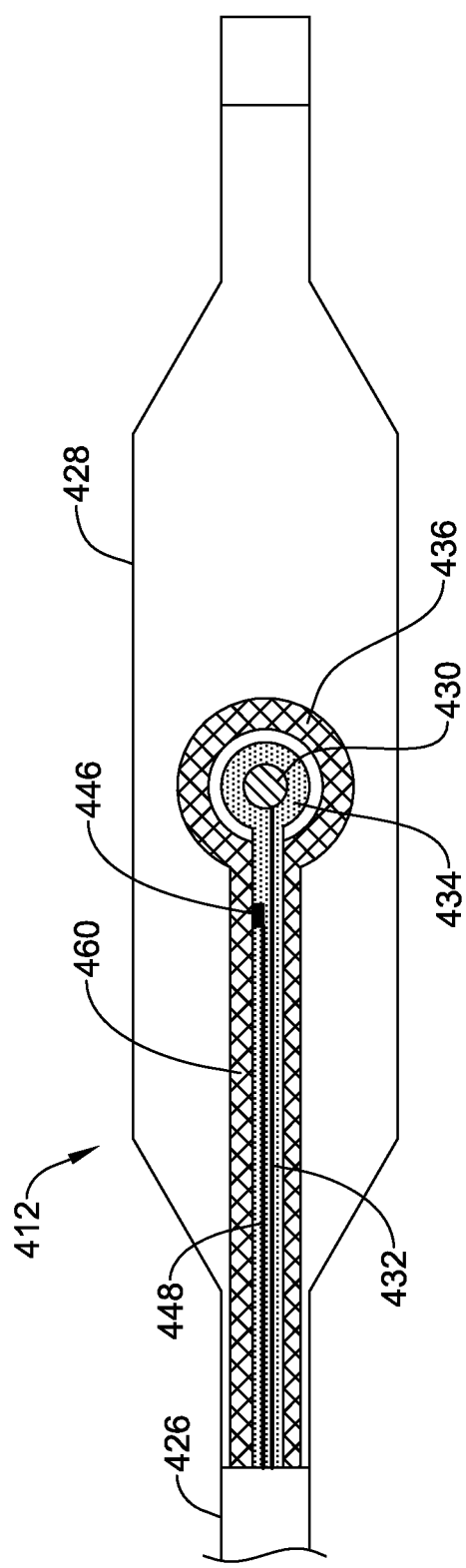
FIG. 7 is side view of another example medical device.

FIG. 7 illustrates another example device 412 that may be similar in form and function to other devices disclosed herein. Device 412 may include catheter shaft 426 having expandable member 428 coupled thereto. Active electrode 430 may be coupled to expandable member 428. Conductive member 432 may be coupled to active electrode 430. Active electrode 430 and conductive member 432 may be disposed along non-conductive layer 434. Temperature sensor 446 may also be coupled to non-conductive layer 434. Conductive member 448 may be coupled to temperature sensor 446. In some embodiments, active electrode 430, temperature sensor 446, and supporting structural components may be coupled to a flex circuit similar to those disclosed herein.

Return electrode 436 may be a ring-like conductive member that is disposed about active electrode 430. In at least some embodiments, common ground electrode 436 may be formed by masking the majority of expandable member 428, leaving regions that will correspond to common ground electrode 436 unmasked, and then applying a conductive coating (e.g., gold, etc.). Device 412 may include a plurality of active electrodes 430 and each active electrode may include a return electrode 436 disposed thereabout. Each of the return electrodes 436 may be connected to a common ground 460.

Figure 8:
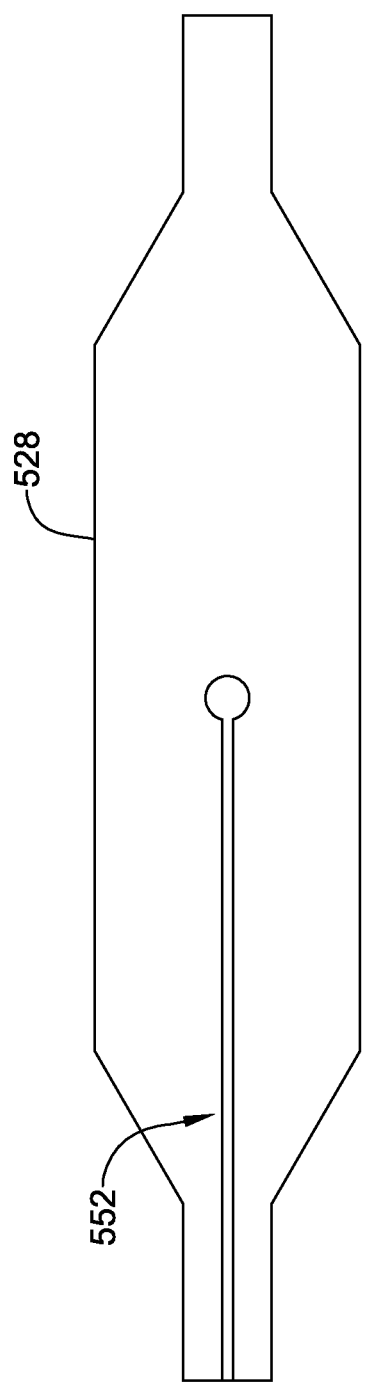
FIG. 8 illustrates a portion of another example medical device.

It can be appreciated that it may be desirable for the overall profile of medical devices (e.g., including those disclosed herein) to be reduced. A portion of an example process for manufacturing a medical device is disclosed in FIGS. 8-10. To the extent applicable, this process may be utilized as part of the process for manufacturing any of the devices disclosed herein. For example, FIG. 8 illustrates a portion of an example expandable member 528 taking the form of a balloon. A groove 552 may be formed in expandable member 528. Groove 552 may be formed by ablating one or more regions or layers of balloon 528. This may include laser ablation. Groove(s) 552 may be formed along one or more different regions of balloon 528 including the waist regions (e.g., proximal and/or distal waists), cone regions (e.g., proximal and/or distal cones), the balloon body, or the like.

Figure 9:
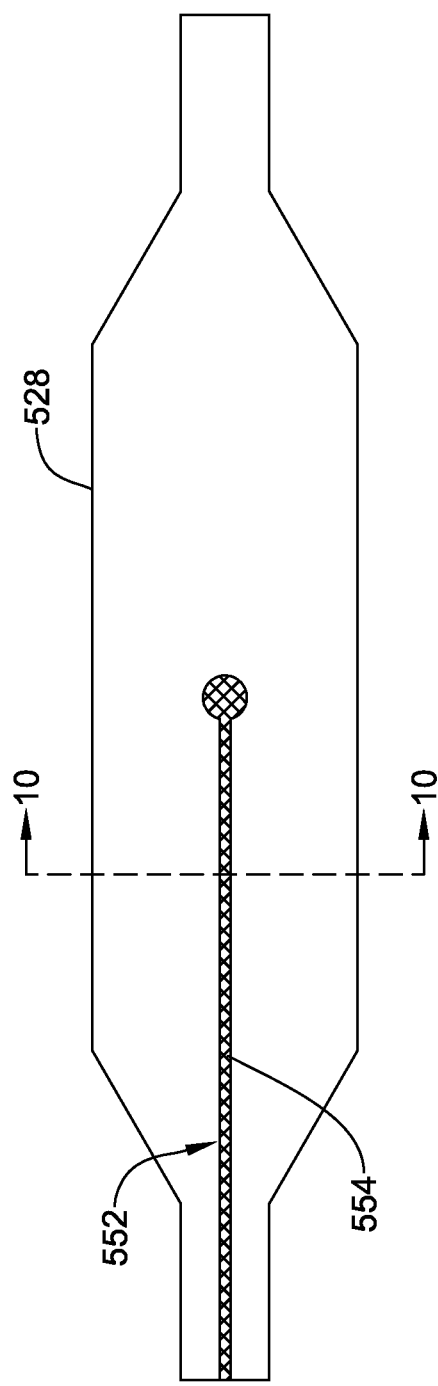
FIG. 9 illustrates the portion of the example medical device shown in FIG. 8 with an active electrode.
Figure 10:
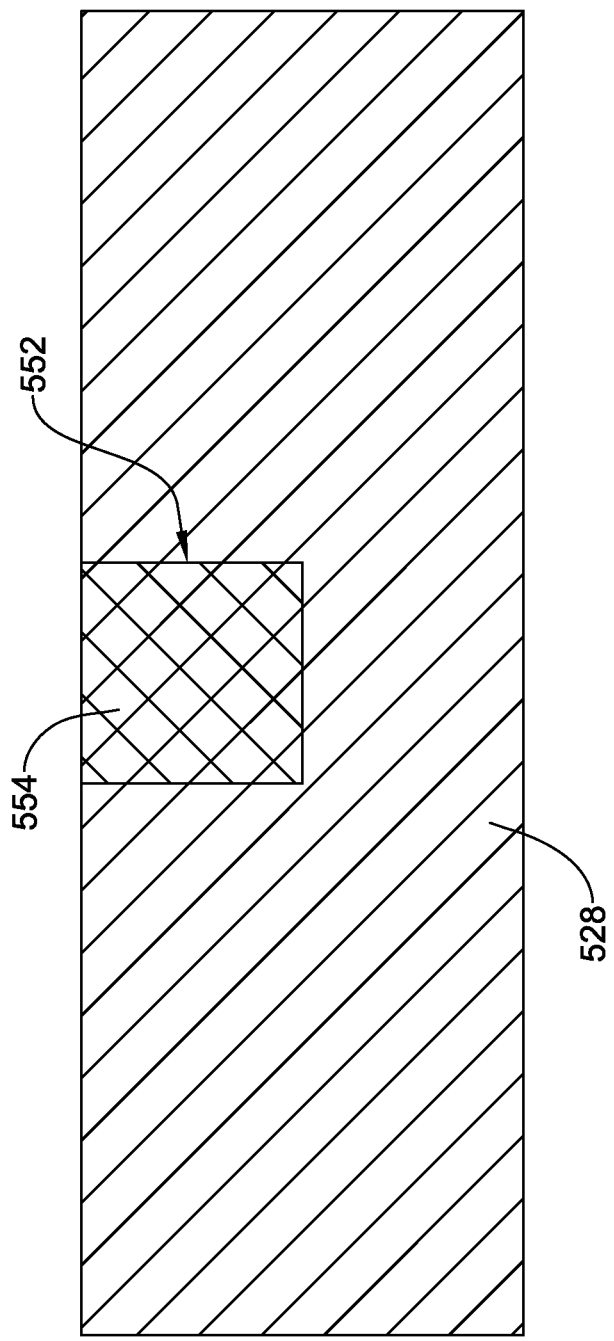
FIG. 10 is a partial cross-sectional view taken through line 10-10 in FIG. 9.

A conductive member 554 may be disposed along groove 552 as illustrated in FIG. 9 and shown in cross-section in FIG. 10. Conductive member 554 may be a portion of an active electrode (e.g., the active electrode itself, a conductive member or trace leading to the active electrode, or the like). Alternatively, conductive member 554 may be part of a ground electrode and/or a common ground electrode. As can be seen, conductive member 554 may be at least partially inserted into groove 552. Because of this, the overall profile of conductive member 554 may be reduced, which may desirably impact the profile of the resultant medical device.

Figure 11:
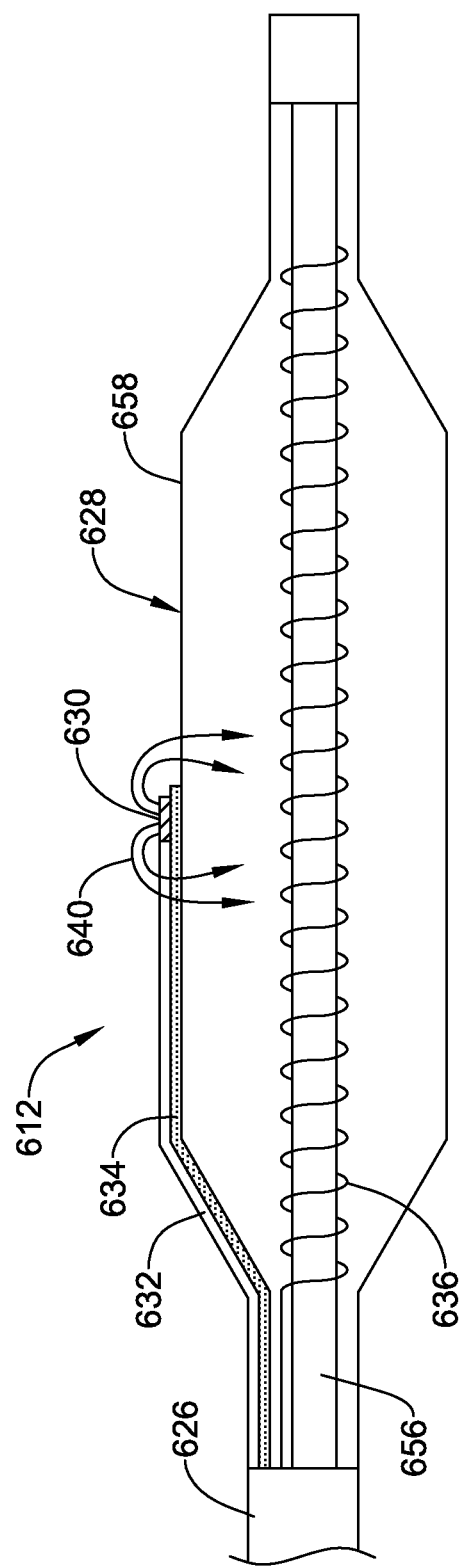
FIG. 11 illustrates a portion of an example medical device.

FIG. 11 illustrates another example device 612 that may be similar in form and function to other devices disclosed herein. Device 612 may include catheter shaft 626 having expandable member 628 coupled thereto. Active electrode 630 may be coupled to expandable member 628. Conductive member 632 may be coupled to active electrode 630. Active electrode 630 and conductive member 632 may be disposed along non-conductive layer 634.

Return electrode 636 may be disposed within expandable member 628. In at least some embodiments, return electrode 636 may be disposed about a shaft or inner member 656 disposed within expandable member 628. One or more conductive regions 658 may be defined along expandable member 628. Conductive regions 658 may be regions of expandable member 628 that are free of non-conductive layer 634. For example, expandable member 628 may be a balloon formed from a hydratable material such as PEBAX MV1074 and conductive regions 658 may be regions of expandable member 628 that are free of non-conductive layer 634. Other materials are contemplated for expandable member 628. A conductive fluid such as saline may be disposed within expandable member 628. Activating active electrode 630 may cause energy to be transmitted therefrom (e.g., into a body tissue). The energy may be conducted via conductive region 658 and the conductive fluid to return electrode 636.

Figure 12:
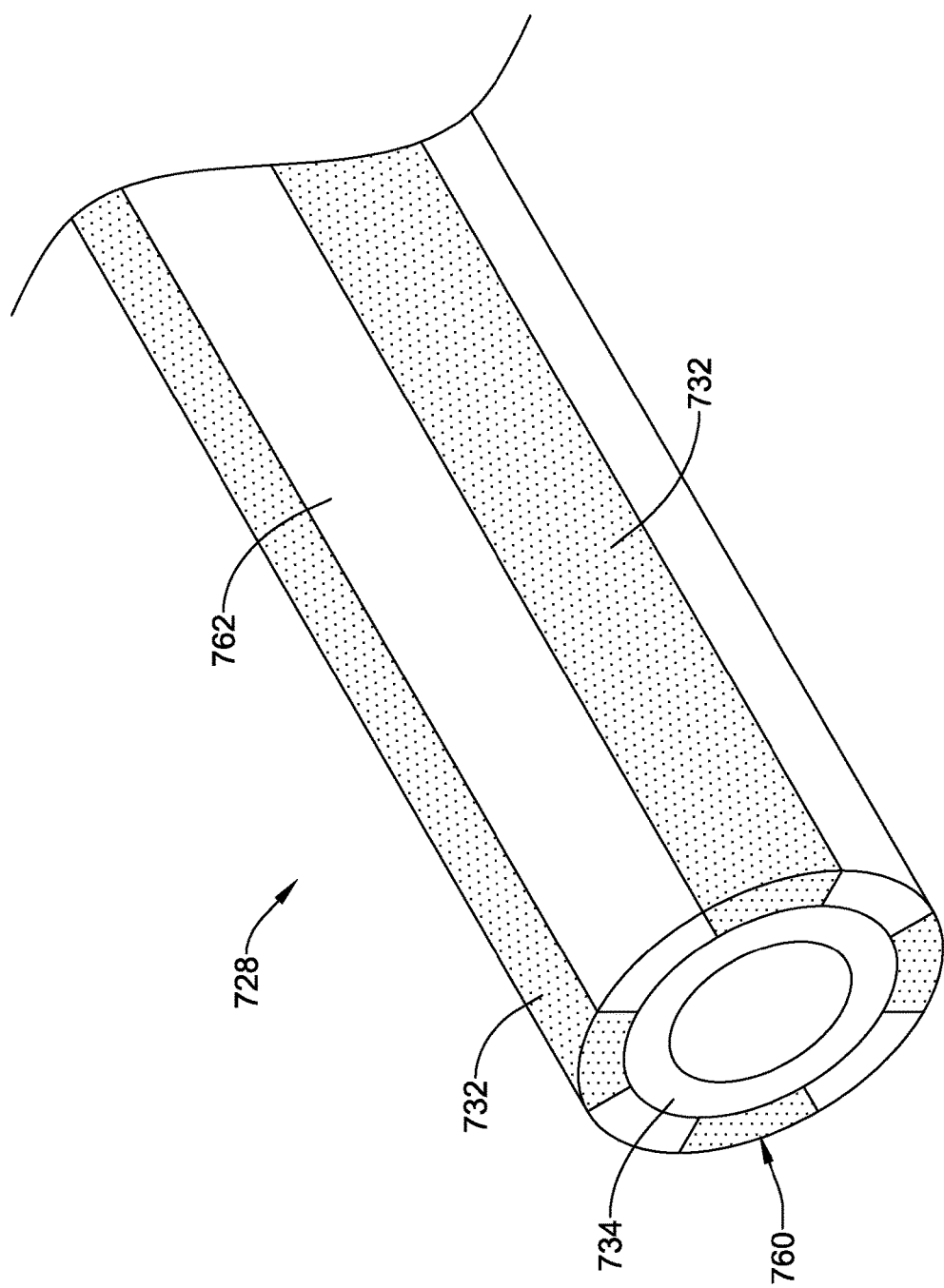
FIG. 12 is a perspective view of a portion of another example medical device.

Other designs are contemplated for medical devices that include an expandable member with one or more conductive regions coupled to electrodes and further are designed to have a lower profile. In some instances, the overall profile of the expandable member can be reduced by incorporating the conductive member directly into the balloon. For example, FIG. 12 illustrates a portion of a tubular member 728 that may be utilized to form an expandable member, catheter shaft, or the like as part of a medical devices (e.g., including any of the medical devices disclosed herein). In general, tubular member 728 may have one or more conductive regions or members 732 incorporated therein. For example, tubular member 728 may include a plurality of layers such as an inner layer 734 and an outer layer 760. Outer layer 760 may include one or more conductive regions 732 and non-conductive regions 762. Conductive regions 732 may be formed from a conductive polymer, a polymer embedded with conductive particles, or the like. Non-conductive regions 762 may be formed from non-conductive materials including, for example, non-conductive polymers (e.g., polyether block amide).

In at least some embodiments, tubular member 728 may be formed by an extrusion process. This may desirably allow for relatively straightforward manufacturing of tubular member 728 with a wide variety of compositions, forms, and configurations. For example, in some embodiments, conductive regions 732 and non-conductive regions 762 may be arranged as longitudinal stripes that extend along tubular member 728. Other configurations are contemplated. After forming tubular member 728 with the desired configuration, tubular member 728 may be utilized as a shaft for a medical device (e.g., a catheter shaft). Alternatively, tubular member 728 may be formed into an expandable member. For example, tubular member 728 may be blow-molded into a balloon. When suitably configured, one or more electrodes (not shown) may be coupled to conductive region 732. Accordingly, a suitable current may be transferred along conductive region 732 to the electrode. Alternatively, conductive regions 732 may be utilized as a ground pathway for other electrodes that may be disposed along a medical device.

Figure 13:
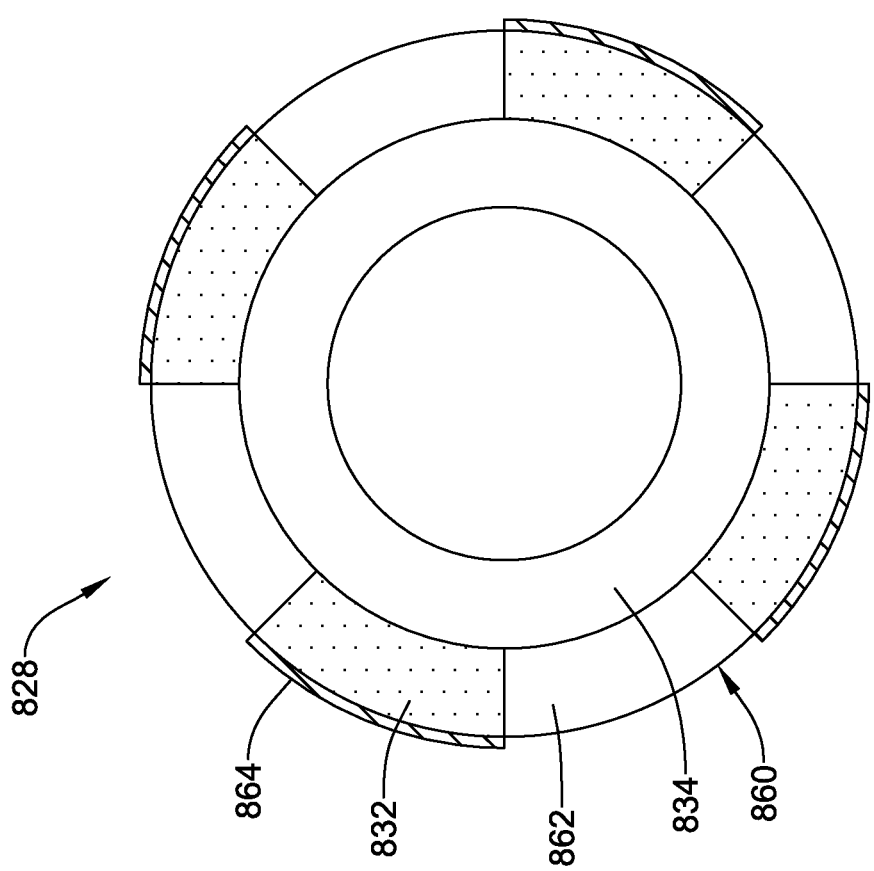
FIG. 13 is an end view of a portion of another example medical device.

FIG. 13 illustrates tubular member 828, which may be similar in form and function to other tubular members (e.g., tubular member 728) disclosed herein. Tubular member 828 may include inner layer 834 and outer layer 860. Outer layer 860 may include conductive regions 832 and non-conductive regions 862. In at least some embodiments, electroplated regions 864 may be disposed along conductive regions 832. Electroplated regions 864 may allow for the level of conductivity to be relatively finely tuned or otherwise improved. The electroplating process could be performed after the extrusion of tubular member 828. Alternatively, electroplating may occur after tubular member 828 is blow-molded into a balloon.

Figure 14:
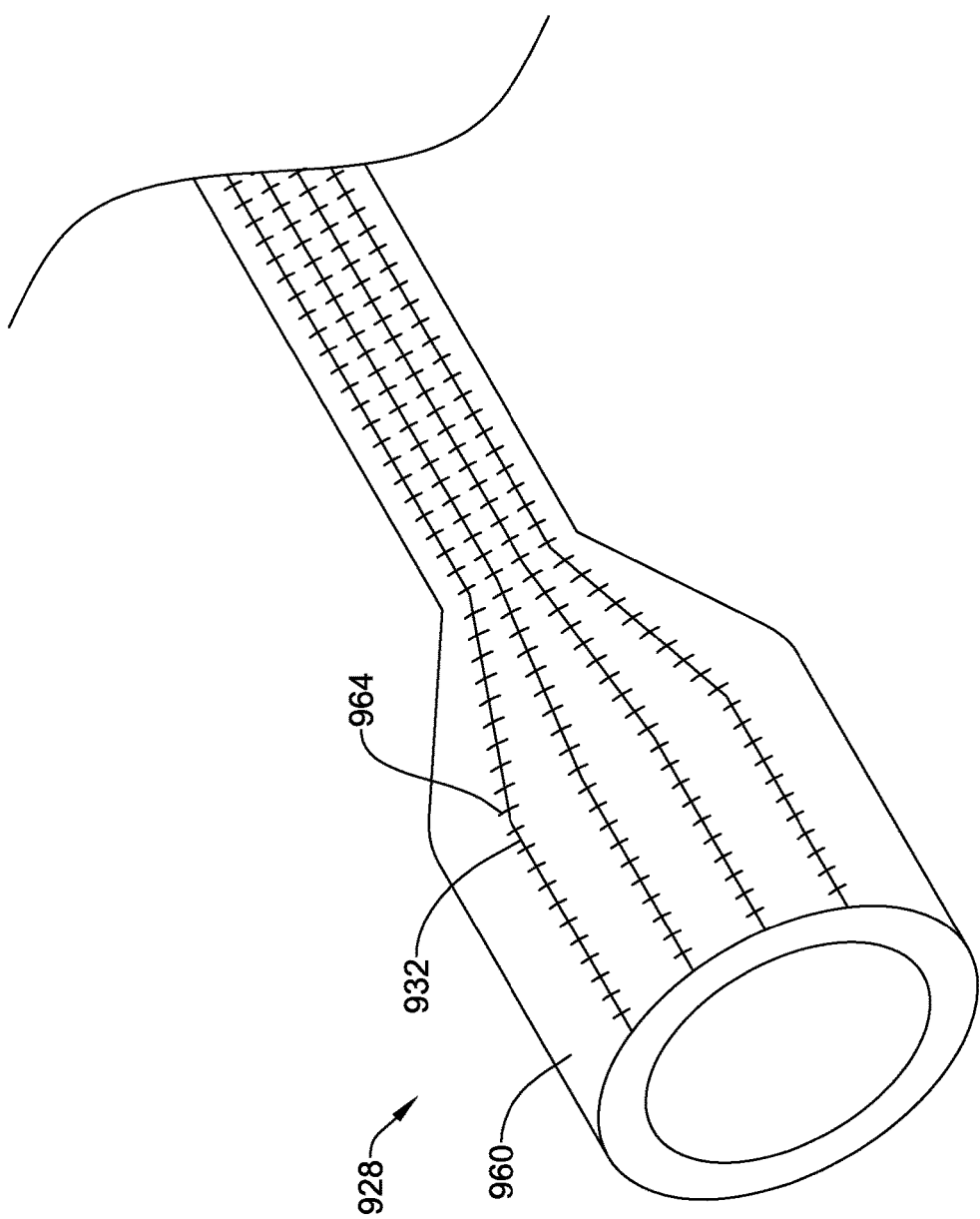
FIG. 14 is a side view of a portion of another example medical device.

FIG. 14 illustrates tubular member 928, which may be similar in form and function to other tubular members disclosed herein. Tubular member 928 may include outer layer 960 with conductive regions 932. Conductive regions 932 may take the form of electrical traces disposed along the surface of tubular member 928, stripes of conductive material similar to conductive regions 732/832, or the like. In some of these and in other embodiments, conductive regions 932 may include a coated (e.g., sputter coated) conductive material (e.g., Pt, Au, Cu, etc.) on outer layer 960 of tubular member 928. For example, Cu or Au may be sputter coated along conductive regions of tubular member 928 (e.g., similar to conductive regions 732/832) to define conductive regions 932. Alternatively, Pt, Au, or the like may be sputter coated directly onto tubular member 928 to define conductive region 932. If desired, one or more electroplated regions 964 may be disposed along conductive regions 932. Electroplated regions 964 may improve conductivity.

Figure 15:
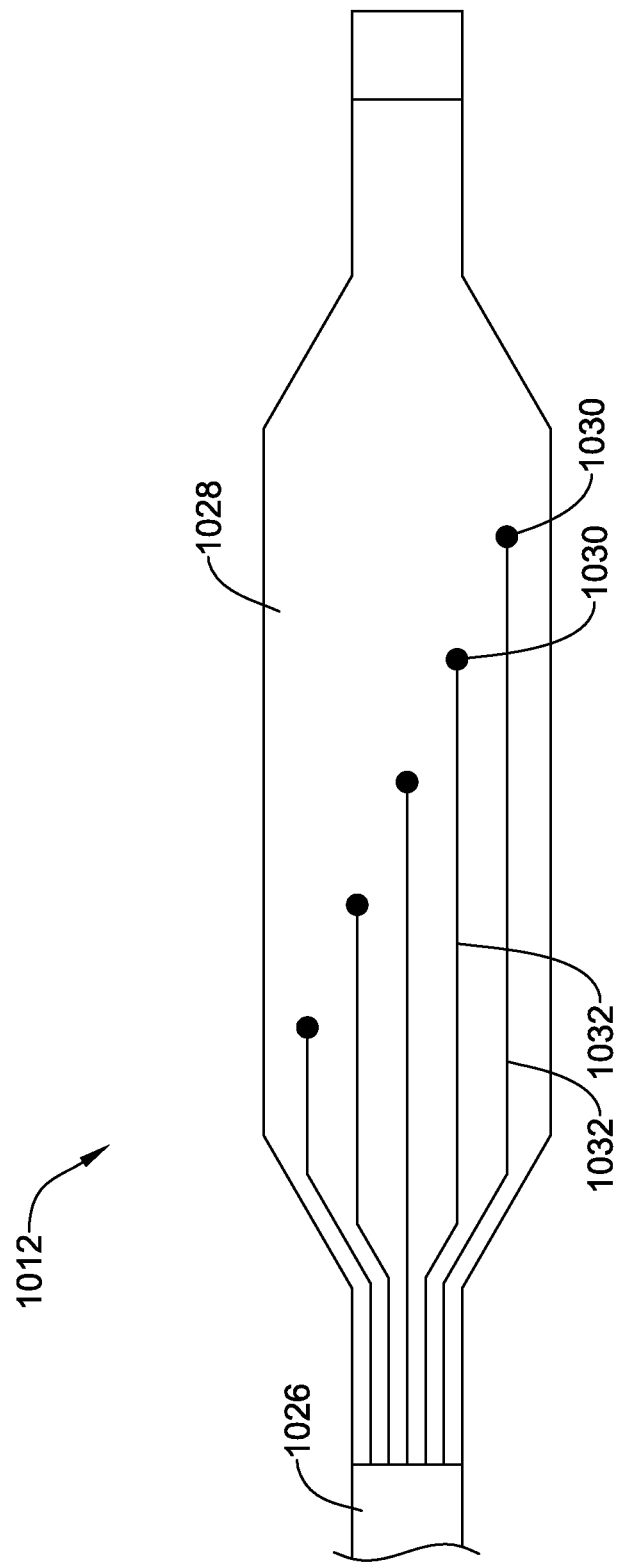
FIG. 15 is a side view of a portion of another example medical device.

FIG. 15 illustrates a portion of another example medical device 1012, which may be similar in form and function to other medical devices disclosed herein. Device 1012 may include catheter shaft 1026 and expandable member 1028 coupled to catheter shaft 1026. One or more conductive members 1032 may be disposed along expandable member 1028. In at least some embodiments, conductive member 1032 may be a conductive adhesive, conductive ink, or the like disposed along expandable member 1028. Conductive member 1032 may be disposed along the outer surface of expandable member 1028 or, in some embodiments, may be partially or fully embedded within expandable member 1028. One or more electrodes 1030 may also be coupled to expandable member 1028.

FIGS. 16-21 illustrate aspects of manufacturing another example medical device 1112, which may be similar to other medical devices disclosed herein, for use in an ablation procedure, such as a renal nerve ablation procedure. Device 1112 may include catheter shaft 1126 and expandable member 1128 coupled to a distal region of catheter shaft 1126. Expandable member 1128 may be an inflatable balloon having a body region 1160, such as a cylindrical body region, a distal cone region 1162 extending distal of body region 1160, a proximal cone region 1164 extending proximal of body region 1160, a distal waist 1166 extending distal of distal cone region 1162, and a proximal waist 1168 extending proximal of proximal cone region 1164.

Distal waist 1166 may be secured (e.g., adhesively or thermally bonded) to a component of catheter shaft 1126, such as a distal end region of an inner tubular member 1127

(see FIG. 16A) of catheter shaft 1126 extending through expandable member 1128, for example. Proximal waist 1168 may be secured (e.g., adhesively or thermally bonded) to a component of catheter shaft 1126, such as a distal end region of an outer tubular member 1125 (see FIG. 16A) of catheter shaft 1126, for example.

Expandable member 1128 (e.g., balloon) may be formed of any desired polymeric material, such as polyimide (PI), polyethylene terephthalate (PET), polyamide (PA), polyether block amide (PEBA), polyethylene (PE), or other desired material. For example, body region 1160, proximal cone region 1164, distal cone region 1162, proximal waist 1168 and distal waist 1166 of expandable member 1128 may be formed as a unitary or monolithic structure of the polymeric material forming expandable member 1128, such as in an extrusion and blow molding process.

During a manufacturing process, a one or more, or a plurality of electrodes may be applied to expandable member 1128, to emit ablation energy to ablate tissue during a medical procedure, as described above. The electrodes may be monopolar or bipolar electrodes, for example. FIGS. 16-21 illustrate exemplary aspects of applying one or more, or a plurality of electrodes to expandable member 1128 of device 1126.

Figure 16:
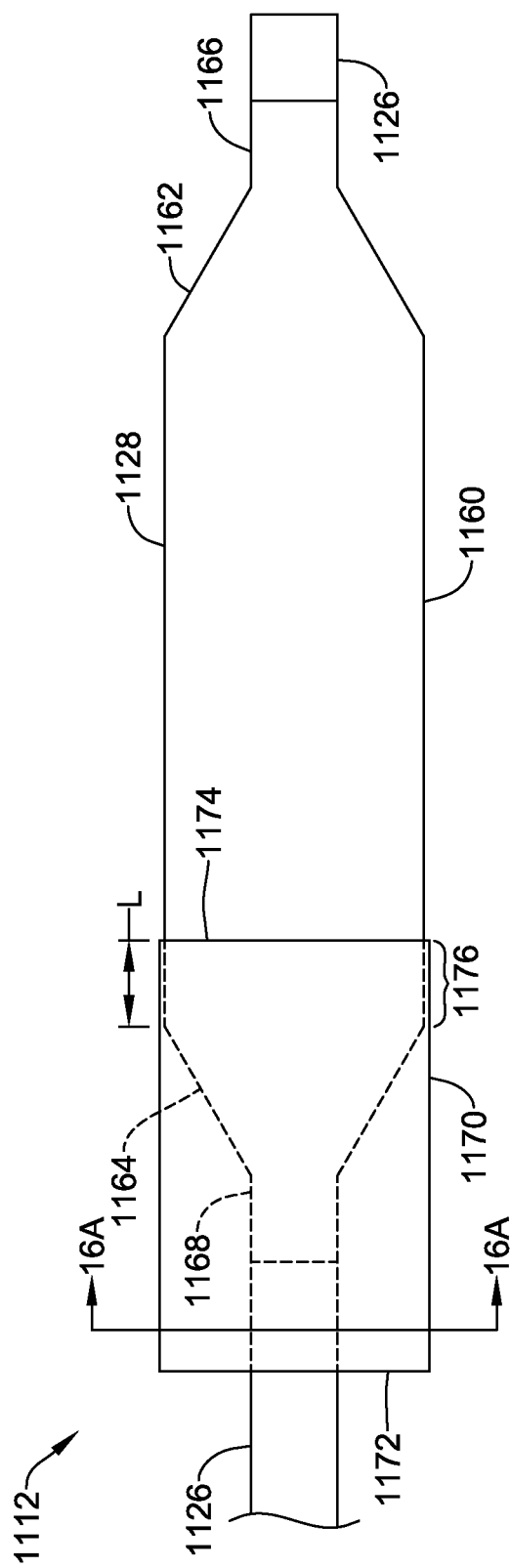
FIGS. 16-21 illustrate aspects of manufacturing a portion of another example medical device.

As shown in FIG. 16, a skirt 1170, which may be a discrete component from expandable member 1128, may be secured to expandable member 1128 and extend proximal of body region 1160 of expandable member 1128. For example, a distal end 1174 of skirt 1170 may be secured (e.g., adhesively or thermally bonded) to body region 1160 of expandable member 1128 with a proximal end 1172 of skirt 1170 not attached to expandable member 1128 or catheter shaft 1126. For example, a distal end region of skirt 1170 may be secured to outer surface of body region 1160 of expandable member 1128 at overlap region 1176, where skirt 1170 overlaps body region 1160. In other embodiments, skirt 1170 may be secured to expandable member 1128 in another fashion. For example, skirt 1170 may be secured to proximal cone region 1164 proximal of body region 1160, if desired.

In some instances, proximal end 1172 may extend to a location proximal of the proximal end of expandable member 1128, such as proximal of the proximal end of proximal waist 1168 of expandable member 1128.

Skirt 1170 may be formed of any desired polymeric material, such as polyimide (PI), polyethylene terephthalate (PET), polyamide (PA), polyether block amide (PEBA), polyethylene (PE), or other desired material. For example, skirt 1170 may be formed of a similar material as the material forming expandable member 1128, or skirt 1170 may be formed of a dissimilar, yet compatible material from the material forming expandable member 1128.

Figure 16A:
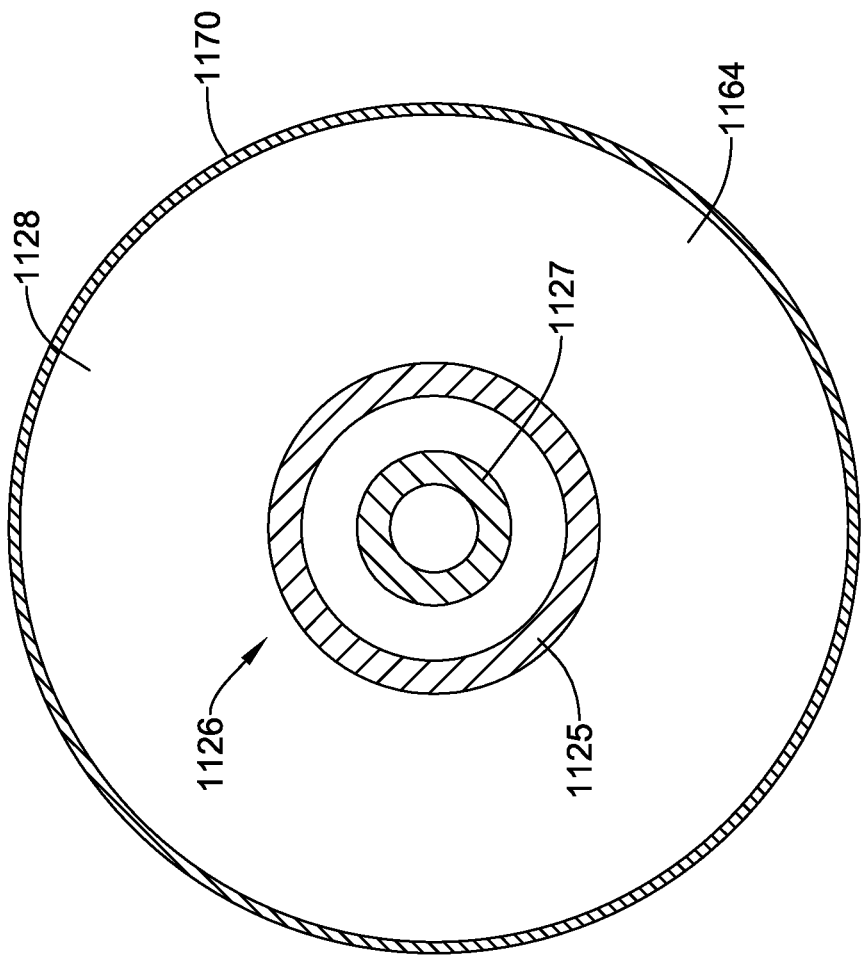
FIG. 16A is a cross-sectional view taken along line 16A-16A in FIG. 16.

In some instances, skirt 1170 may be an annular member as shown in FIG. 16A, having a distal portion circumferentially surrounding expandable member 1128, such as circumferentially surrounding body region 1160 of expandable member at overlap region 1176. In other instances, skirt 1170 may be one or more longitudinal strips of material, such as a longitudinal strip of material having a distal end portion secured to expandable member 1128 and extending proximally therefrom. In some instances, skirt 1170 may include multiple discrete longitudinal strips of material secured to expandable member 1128 at spaced apart locations around the circumference of expandable member 1128 and extend proximally therefrom. In some instances, the multiple discrete longitudinal strips of material may be arranged symmetrically or asymmetrically around the circumference of expandable member 1128. In other instances, skirt 1170 may include one or more, or a plurality of longitudinal strips of material extending proximally from an annular portion circumferentially surrounding expandable member 1128 and secured to body region 1160 at overlap region 1176.

In some instances, skirt 1170 may extend generally parallel to outer surface 1160 of body region of expandable member 1128, such that outer surface of skirt 1170 may be substantially equidistant from the central longitudinal axis of expandable member 1128 as outer surface of body region 1160 of expandable member 1128. For example, in instances in which skirt 1170 is an annular member, skirt 1170 may have a diameter substantially equal to the diameter of body region of expandable member 1128. As shown in FIG. 16A, a proximal portion of skirt 1170 extending proximal of body region 1160 of expandable member 1128 may be spaced radially away from proximal waist 1168 and catheter shaft 1126.

Figure 17:
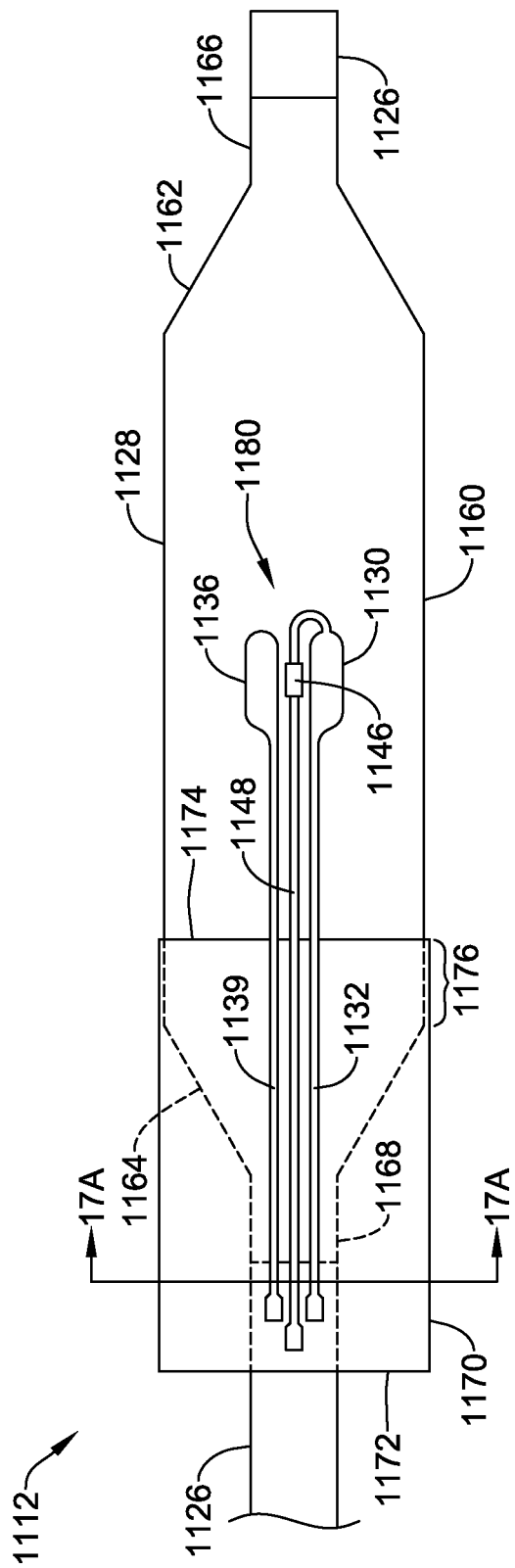

Turning to FIG. 17, an electrode assembly 1180 (e.g., a bipolar electrode pair) may be applied directly to outer surface of body region 1160 of expandable member 1128. For example, an active electrode 1130, which may be an ablation electrode capable of delivering ablation energy to tissue (e.g., tissue positioned adjacent to a blood vessel such as renal nerves positioned adjacent to a renal artery), may be formed on outer surface of body region 1160 of expandable member 1128. Furthermore, a return or ground electrode 1136, providing a return electrical pathway from the active electrode 1130, may be formed on outer surface of body region 1160 at a desired spaced relationship with active electrode 1130.

Furthermore, in some instances, electrode assembly 1180 may include a temperature sensor 1146 applied to outer surface of body region 1160. Temperature sensor 1146 may be positioned between active electrode 1130 and return or ground electrode 1136, or at another desired location. Temperature sensor 1146 may include a thermistor, thermocouple, or any other suitable temperature sensor.

A first conductive member 1132 may additionally be applied directly to outer surface of body region 1160 and extend proximally from active electrode 1130 to provide an electrical pathway to active electrode 1130. Conductive member 1132 may take the form of a conductive trace, for example. In some instances, conductive member 1132 may be formed contemporaneously with active electrode 1130. Conductive member 1132 may extend proximally from active electrode 1130 along and be directly attached to body region 1160 and along and be directly attached to skirt 1170. Accordingly, conductive member 1132 may extend continuously from body region 1160 proximate active electrode 1130 to skirt 1170 across overlap region 1176. For example, conductive member 1132 may extend continuously from active electrode 1130 on body region 1160 to a location on skirt 1170 proximal of proximal end of expandable member 1128 in some instances.

A second conductive member 1139 may additionally be applied directly to outer surface of body region 1160 and extend proximally from return or ground electrode 1136 to provide an electrical pathway from ground or return electrode 1136. Conductive member 1139 may take the form of a conductive trace, for example. In some instances, conductive member 1139 may be formed contemporaneously with ground or return electrode 1136. Conductive member 1139 may extend proximally from ground or return electrode 1136 along and be directly attached to body region 1160 and along and be directly attached to skirt 1170. Accordingly, conductive member 1139 may extend continuously from body region 1160 proximate return or ground electrode 1136 to skirt 1170 across overlap region 1176. For example, conductive member 1139 may extend continuously from return or ground electrode 1139 on body region 1160 to a location on skirt 1170 proximal of proximal end of expandable member 1128 in some instances.

Furthermore, in embodiments including temperature sensor 1146, a third conductive member 1148 may additionally be applied directly to outer surface of body region 1160 and extend from active electrode 1130 to temperature sensor 1146 and proximally from temperature sensor 1146 to provide an electrical pathway to temperature sensor 1146. Conductive member 1148 may take the form of a conductive trace, for example. In some instances, conductive member 1148 may be formed contemporaneously with active electrode 1130. Conductive member 1148 may extend proximally from temperature sensor 1146 along and be directly attached to body region 1160 and along and be directly attached to skirt 1170. Accordingly, conductive member 1148 may extend continuously from the body region 1160 proximate temperature sensor 1146 to skirt 1170 across overlap region 1176. For example, conductive member 1148 may extend continuously from temperature sensor 1146 on body region 1160 to a location on skirt 1170 proximal of proximal end of expandable member 1128 in some instances.

Active electrode 1130 and return electrode 1136 of bipolar electrode assembly 1180, as well as first, second and third conductive members 1132, 1139, 1148 may be applied directly onto the outer surface of body region 1160 of expandable member 1128, with first, second and third conductive members 1132, 1139, 1148 extending proximally therefrom and applied directly onto the outer surface of skirt 1170. In some instances, expandable member 1128 may be masked and then sputter coated (e.g., vapor deposition process) or plated with an electrically conductive material (e.g., gold, copper, platinum, etc.) to form electrodes 1130, 1136 and conductive members 1132, 1139, 1148, for example. In some instances, the mask may then be removed and additional layers or coatings of an electrically conductive material may be applied to increase the thickness, current capacity and/or durability of electrodes 1130, 1136 and/or conductive members 1132, 1139, 1148. For example, additional layers of an electrically conductive material may be plated over an initial sputter coated layer of an electrically conductive material. In other embodiments, a photo etching process, electrodepositing process, or other process may be used to apply electrode assembly 1180 (i.e., the circuit) including electrodes 1130, 1136 and/or conductive members 1132, 1139, 1148 directly to expandable member 1128 and skirt 1170. In yet other embodiments, a channel may be formed along expandable member 1128 and skirt 1170, such as in a laser ablation process, and subsequently an electrically conductive material may be disposed in the channel, such as during a vapor deposition process, to form electrode assembly 1180 including electrodes 1130, 1136 and/or conductive members 1132, 1139, 1148, or a portion thereof.

As shown in FIG. 17, in some embodiments, electrode assembly 1180 (i.e., the circuit) including electrodes 1130, 1136 and/or conductive members 1132, 1139, 1148 may be applied directly to expandable member 1128 and skirt 1170 with expandable member 1128 in an expanded state. For example, when expandable member 1128 is an inflatable balloon electrode assembly 1180 (i.e., the circuit) including electrodes 1130, 1136 and/or conductive members 1132, 1139, 1148 may be applied directly to expandable member 1128 and skirt 1170 with expandable member 1128 in an inflated state. In other embodiments, electrode assembly 1180 may be applied with expandable member 1128 in a collapsed or deflated state, if desired. As shown in FIG. 17A, conductive members 1132, 1139, 1148 may be directly applied to skirt 1170 with proximal portion of skirt 1170 (e.g., portion extending proximal of body region 1160 of expandable member 1128) positioned radially outward away from catheter shaft 1128 and proximal waist 1168.

Figure 18:
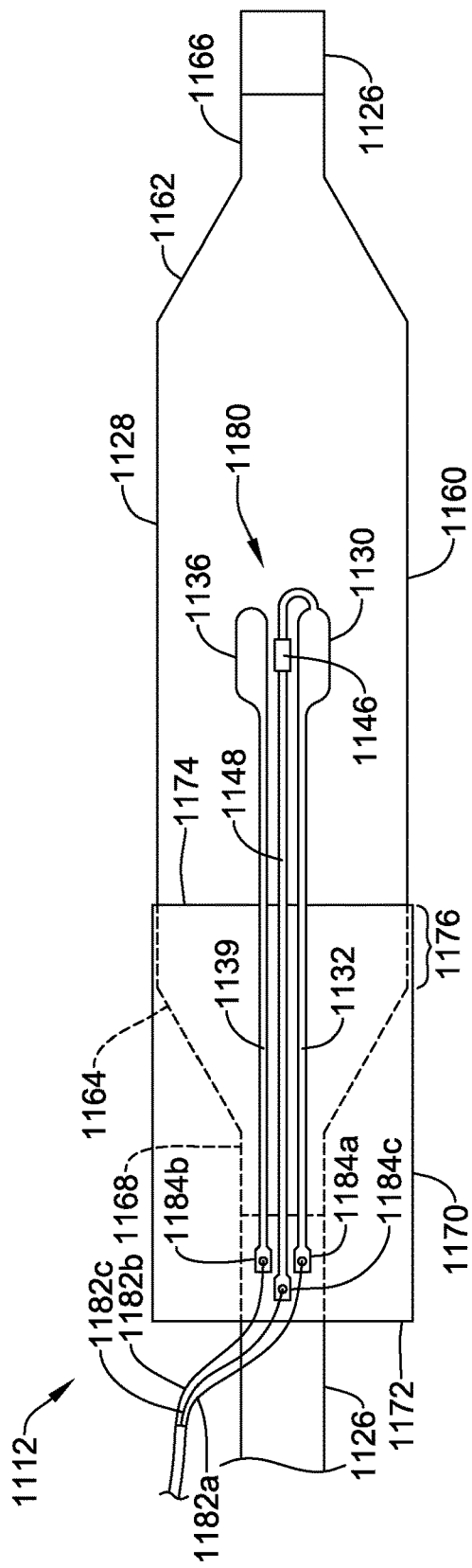

Turning to FIG. 18, electrically conductive wires 1182 may then be connected to a proximal end of each of conductive members 1132, 1139, 1148 proximate the proximal end of skirt 1170. For example, a first electrically conductive wire 1182a may be connected to proximal end of first conductive member 1132 at a first termination point 1184a, a second electrically conductive wire 1182b may be connected to proximal end of second conductive member 1139 at a second termination point 1184b, and a third electrically conductive wire 1182c may be connected to proximal end of third conductive member 1148 at a third termination point 1184c. Conductive wires 1182 may be connected to conductive members 1132, 1139, 1148 at termination points 1184 such as by soldering, ultrasonic welding, stamping, or other technique, for example.

The process of connecting wires 1182 to conductive members 1132, 1139, 1148 at termination points 1184 may require the application of heat, such as during a soldering process. In such instances, the portion of skirt 1170 underlying termination points 1184 (e.g., the proximal portion of skirt 1170) may be held longitudinally away from expandable member 1128 and/or radially away from catheter shaft 1126, isolating and/or insulating expandable member 1128 and/or catheter shaft 1126 from the heating process, and thus keeping the heat away from expandable member 1128 and/or catheter shaft 1126 to avoid inadvertent damage to expandable member 1128 and/or catheter shaft 1126 while making the electrical connections. For example, termination points 1184 formed when connecting wire 1182 to conductive members 1132, 1139, 1148 may be spaced radially outward away from the outer surface of catheter shaft 1126 to avoid inadvertent damage to catheter shaft 1126 and may be located proximal of expandable member 1128, such as proximal of body region 1160, proximal cone region 1164 and proximal waist 1168 to avoid inadvertent damage to expandable member 1128.

In some instances, a fixture or substrate (not shown) may be positioned within proximal portion of skirt 1170 between inner surface of skirt 1170 and catheter shaft 1126, proximal balloon waist 1168 and/or proximal cone region 1164 to support skirt 1170 while applying conductive members 1132, 1139, 1148 onto outer surface of skirt 1170 and/or connecting electrical wires 1182 at termination points 1184. In some instances, the fixture or substrate may maintain skirt 1170 in a cylindrical configuration of approximately the same diameter as expandable member 1128 (e.g., inflated balloon) while applying conductive members 1132, 1139, 1148 onto outer surface of skirt 1170 and/or connecting electrical wires 1182 at termination points 1184.

Conductive wires 1182a, 1182b, 1182c, which may be insulated from each other, may be coupled to or be a region of conductive member 18 and, ultimately, may be coupled to generator 16. Thus, a suitable energy (e.g., RF energy) may be delivered to electrode assembly 1180 from generator 16 via conductive wires 1182a, 1182b, 1182c.

Figure 19:
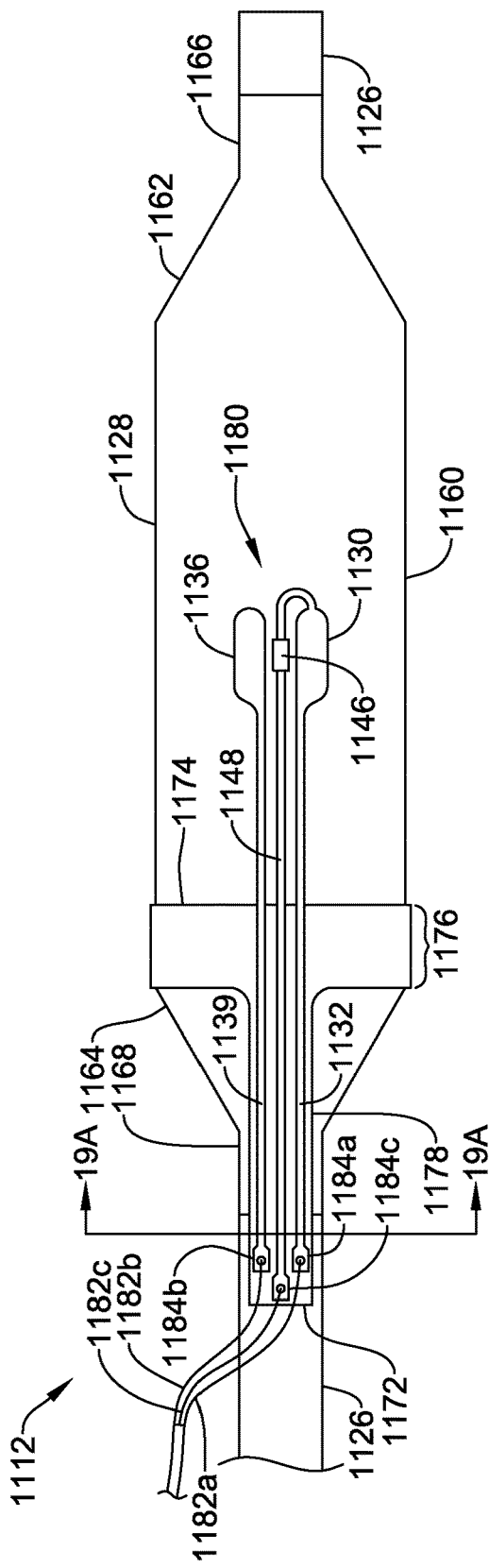

As shown in FIG. 19, excess portions of skirt 1170 may be removed, leaving strips 1178 of skirt 1170 underlying conductive members 1132, 1139, 1148 and termination points 1184 attached to expandable member 1128. For example, as shown in FIG. 19, first, second and third conductive members 1132, 1139, 1148 of electrode assembly 1180 may be attached to a single strip 1178 of material of skirt 1170, extending proximally from body region 1160 of expandable member 1128 from overlap region 1176.

Figure 19A:
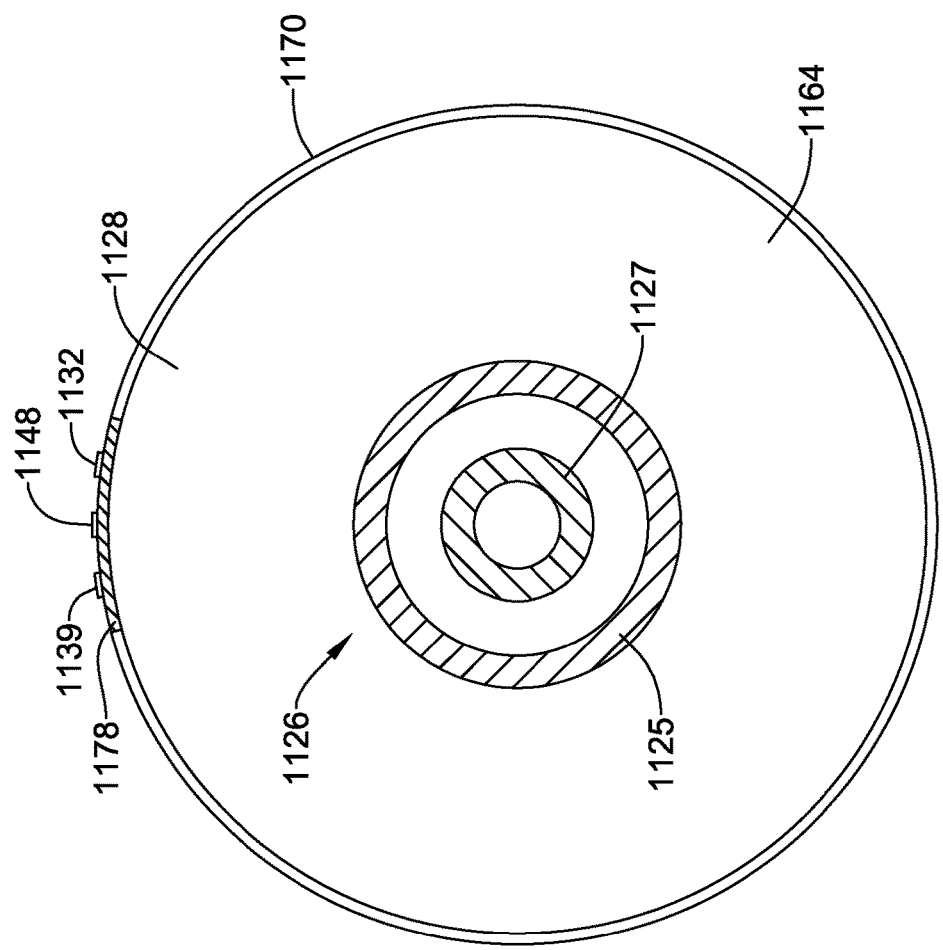
FIG. 19A is a cross-sectional view taken along line 19A-19A in FIG. 19.
Figure 19B:
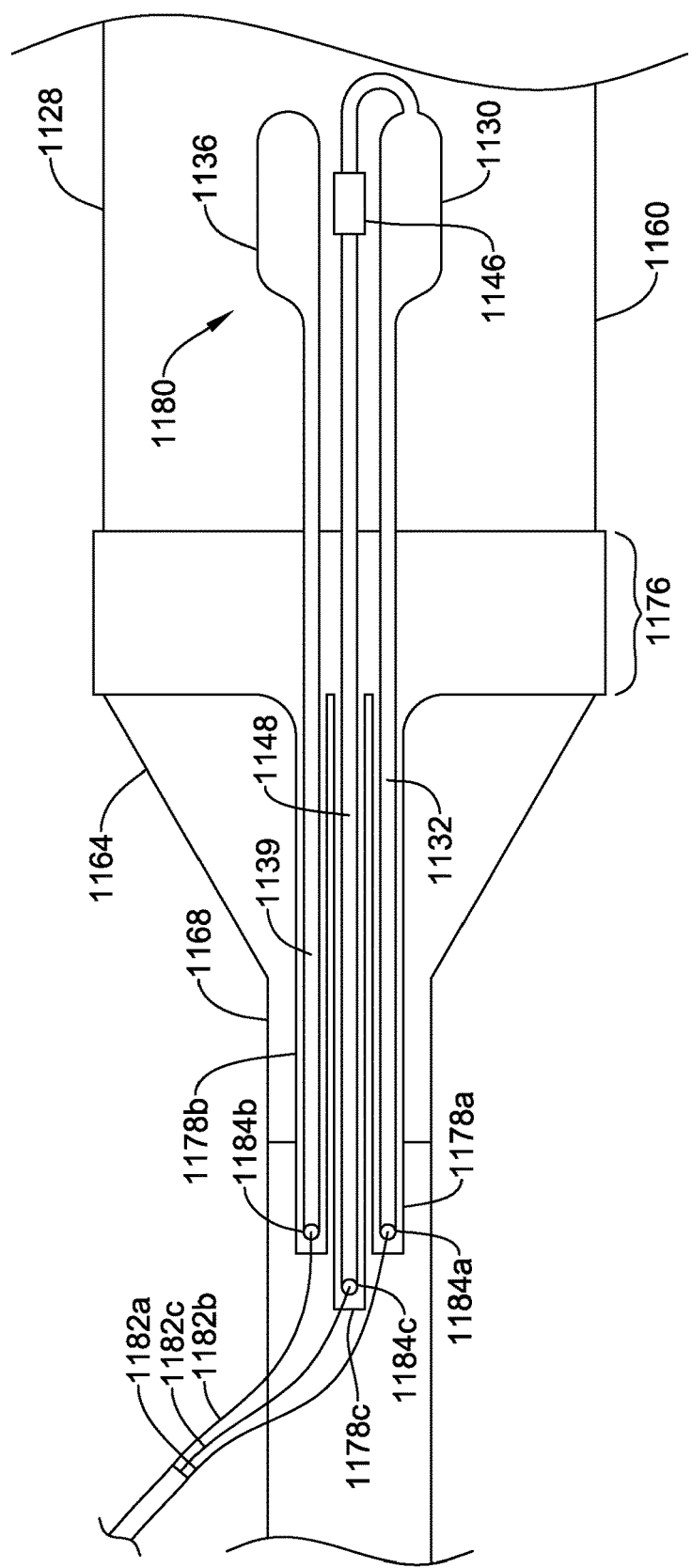
FIG. 19B illustrates an alternative manufacturing aspect in forming an example medical device.

Alternatively, as shown in FIG. 19B, one or more, or each of first, second and third conductive members 1132, 1139, 1148 of electrode assembly 1180 may be attached to a separate strip 1178 of material of skirt 1170 spaced apart from adjacent strips. For instance, first conductive member 1132 and first termination point 1184a may be attached to a first strip 1178a of material of skirt 1170 extending proximally from overlap region 1176 and body region 1160 of expandable member 1128, second conductive member 1139 and second termination point 1184b may be attached to a second strip 1178b of material of skirt 1170 extending proximally from overlap region 1176 and body region 1160 of expandable member 1128, and third conductive member 1148 and third termination point 1184c may be attached to a third strip 1178c of material of skirt 1170 extending proximally from overlap region 1176 and body region 1160 of expandable member 1128. Slits or slots extending distally from the proximal end of strips 1178a, 1178b, 1178c toward overlap region 1178 may separate the first, second and third strips 1178a, 1178b, 1178c.

Excess material of skirt 1170 may be removed or trimmed away by any desired means. For example, in some instances a laser ablation process may be used to cut away excess material of skirt 1170, leaving strips 1178 of material attached to and extending proximally from body region 1160 of expandable member 1128. In other embodiments, another cutting process may be used to remove the excess material of skirt 1170.

FIG. 19A illustrates strip 1178 of material having conductive members 1132, 1139, 1148 applied thereto positioned radially away from catheter shaft 1126. Strip 1178 may be a segment of annular member of skirt 1170 after one or more segments of annular member of skirt 1170 are excised. In embodiments in which multiple electrode assemblies 1180 are mounted on expandable member 1128, multiple strips 1178 (e.g., multiple segments of annular member of skirt 1170) may extend proximal of body region 1160 after a plurality of segments of annular member of skirt 1170 are excised.

In other embodiments, skirt 1170 may be or include one or more, or a plurality of longitudinal strips 1178 of material when secured to body region 1160 of expandable member. Accordingly, in such instances, trimming away excess material may be unnecessary.

As shown in FIG. 19, excess material of skirt 1170 may be removed from proximal portion of skirt 1170 located proximal of body region 1160 of expandable member 1128. For example, segments of excess material of skirt 1170 between strips 1178 having conductive members 1132, 1139, 1148 thereon may be removed from proximal end 1172 of skirt 1170 to proximate overlap region 1176.

Figure 20:
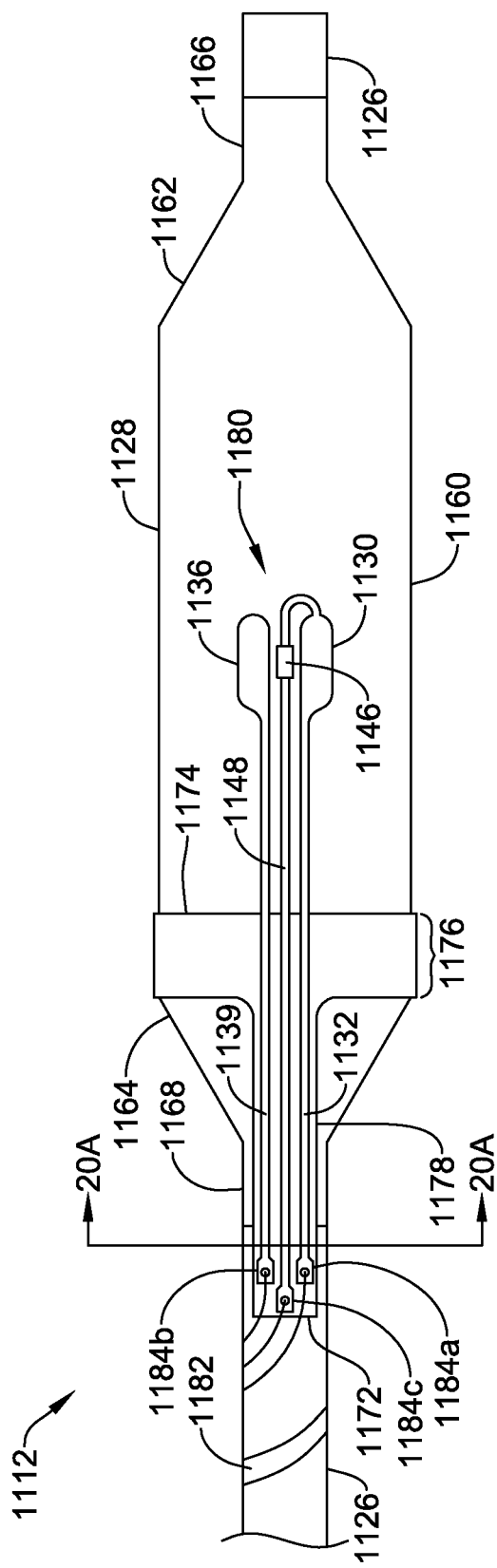
Figure 20A:
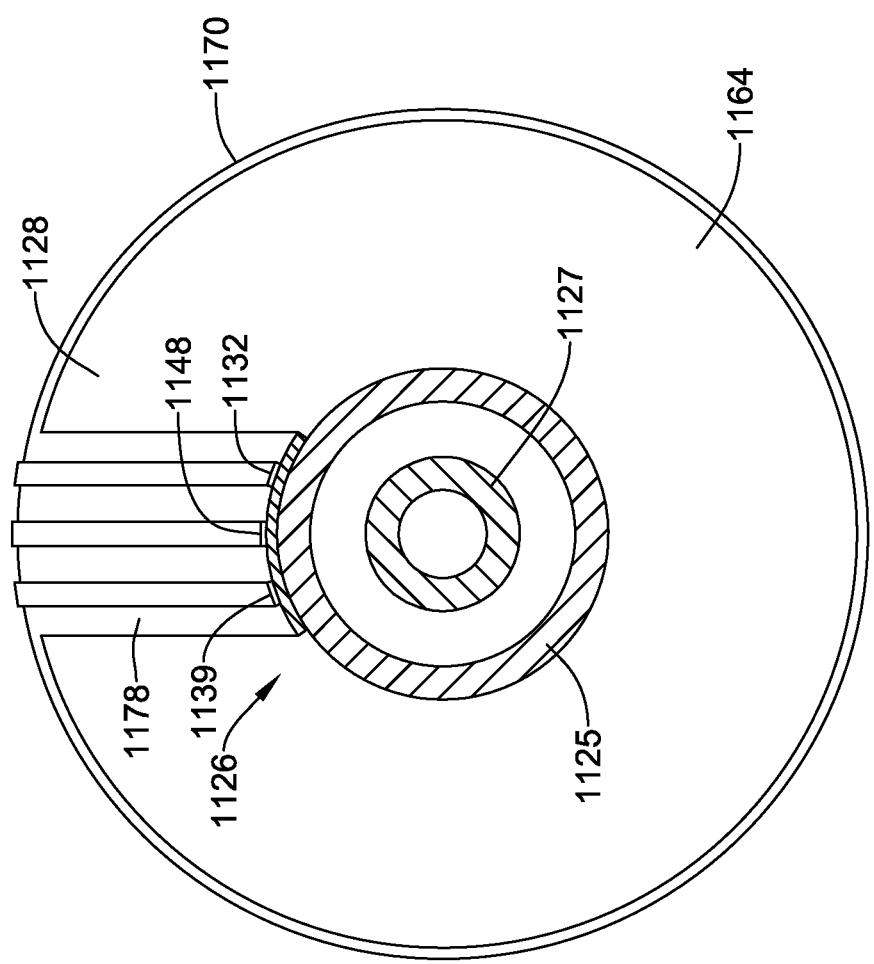
FIG. 20A is a cross-sectional view taken along line 20A-20A in FIG. 20.

Turning to FIG. 20, strip 1178 of material of skirt 1170 having conductive members 1132, 1139, 1148 thereon and extending proximal of body region 1160 of expandable member 1128 may then be secured to proximal cone region 1164, proximal waist 1168 and/or catheter shaft 1126. For example, strip 1178 of material of skirt 1170 may be adhesively bonded to outer surface of proximal cone region 1164, outer surface of proximal waist 1168 and/or outer surface of catheter shaft 1126, with conductive wires 1182 extending proximally along catheter shaft 1126. FIG. 20A, illustrates, strip 1178 of skirt 1170 moved radially inward and secured to catheter shaft 1126, with strip 1178 following along proximal cone region 1164 and proximal waist 1168 of expandable member 1128. Accordingly, proximal portion of strip 1178 of skirt 1170 proximal of overlap region 1176 may be brought into contact with proximal cone region 1164, proximal waist 1168 and/or catheter shaft 1126 and secured thereto. Thus, proximal portion of strip 1178 having termination points 1184 thereon, may only be brought into contact with catheter shaft 1126 and/or proximal waist 1168 after conductive members 1132, 1139, 1148 and termination points 1184 attaching conductive wires 1182 to conductive members 1132, 1139, 1148 have been applied to strip 1178 of material of skirt 1170.

Figure 21:
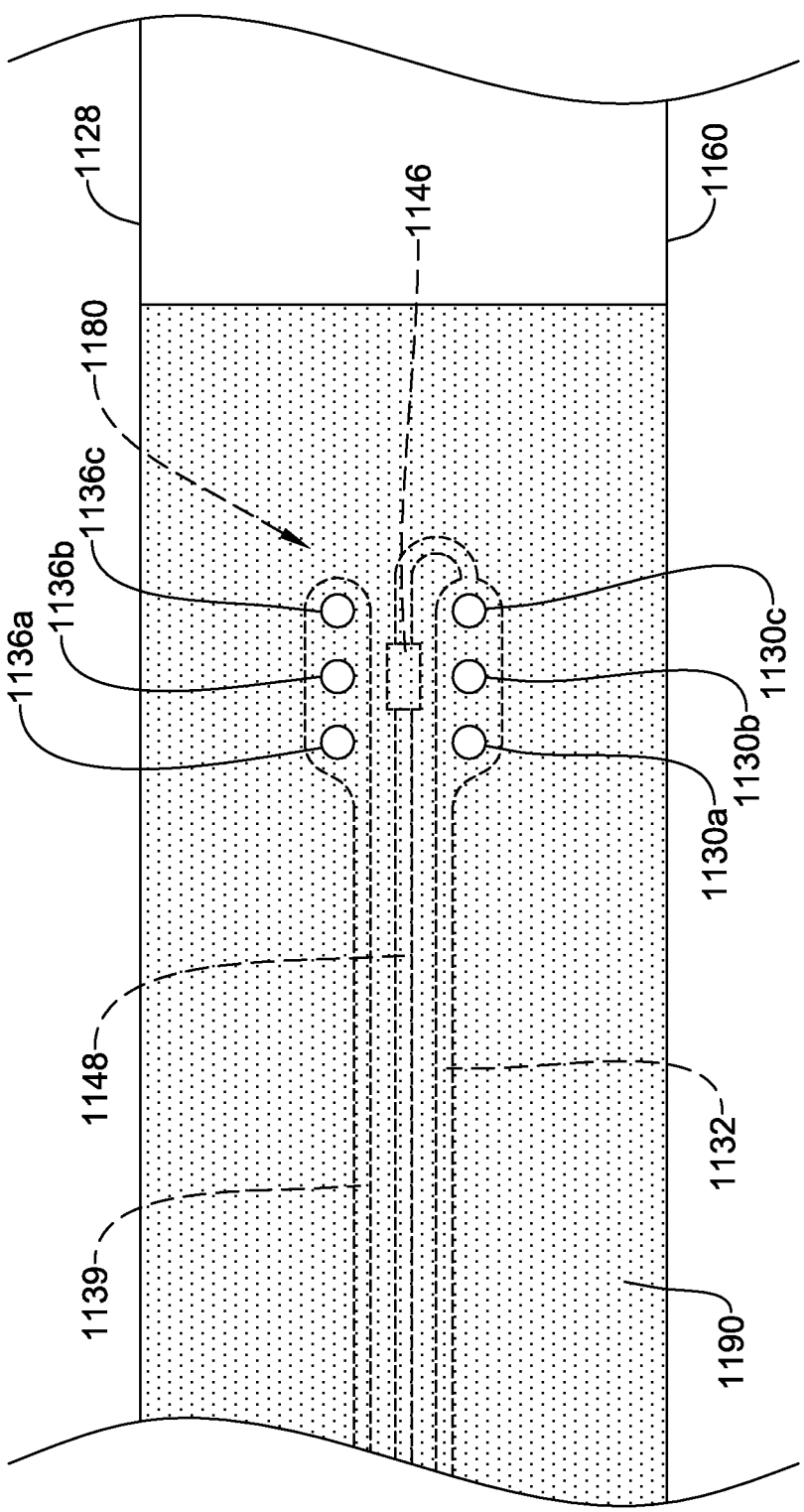

As shown in FIG. 21, a non-conductive layer 1190 (e.g., an electrically insulating mask) may be placed over conductive members 1132, 1139, 1148 along expandable member and strip 1178 of material of skirt 1170 to electrically insulate conductive members 1132, 1139, 1148 from one another and body tissue during use. In some instances, non-conductive layer 1190 may cover a portion of active electrode 1130, while leaving one or more portions of active electrode 1130 uncovered. For example, as shown in FIG. 21, uncovered portions of active electrode 1130 may effectively provide a first active electrode 1130a, a second active electrode 1130b and/or a third active electrode 1130c, for example. Additionally or alternatively, in some instances, non-conductive layer 1190 may cover a portion of ground or return electrode 1136, while leaving one or more portions of ground or return electrode 1136 uncovered. For example, as shown in FIG. 21, uncovered portions of ground or return electrode 1136 may effectively provide a first ground or return electrode 1136a, a second ground or return electrode 1136b and/or a third ground or return electrode 1136c, for example.

In some instances, active electrode 1130 or portions thereof, and/or ground or return electrode 1136, or portions thereof, may be masked prior to applying non-conductive layer 1190, and then the mask may subsequently be removed to expose active electrode 1130 and/or ground or return electrode 1136. In other instances, non-conductive layer 1190 may be removed (e.g., chemically etched, photo etched, ablated, etc.) to uncover active electrode 1130 and/or ground or return electrode 1136, or portions thereof.

Active electrode 1130 and ground or return electrode 1136 may function as a bipolar electrode pair. For instance, first active electrode 1130a and first ground or return electrode 1136a may function as a first bipolar electrode pair, second active electrode 1130b and second ground or return electrode 1136b may function as a second bipolar electrode pair, and/or third active electrode 1130c and third ground or return electrode 1136c may function as a third bipolar electrode pair, for example.

Non-conductive layer 1190 may fluidly seal and electrically insulate conductive members 1132, 1139, 1138 between non-conductive layer 1190 and body region 1160 of expandable member 1128 and skirt 1170. In some instances, non-conductive layer 1190 may be a non-conductive polymer, such as polyimide or poly ether block amide (PEBA) or another polymeric material, for example. In some embodiments, non-conductive layer 1190 may be about 0.01 millimeters to about 0.02 millimeters thick, for example. In some instances, non-conductive layer 1190 may be an annular heat shrink sleeve heat shrunk around body region 1160, overlap region 1176, and strip 1178 of skirt 1170. In other instances, non-conductive layer 1190 may be spray coated, dip coated or otherwise applied to body region 1160, overlap region 1176, and strip 1178 of skirt 1170. For example, non-conductive layer 1190 may be a complete or partial polymer coating, such as polytetrafluoroethylene (PTFE) or silicone.

Figure 22:
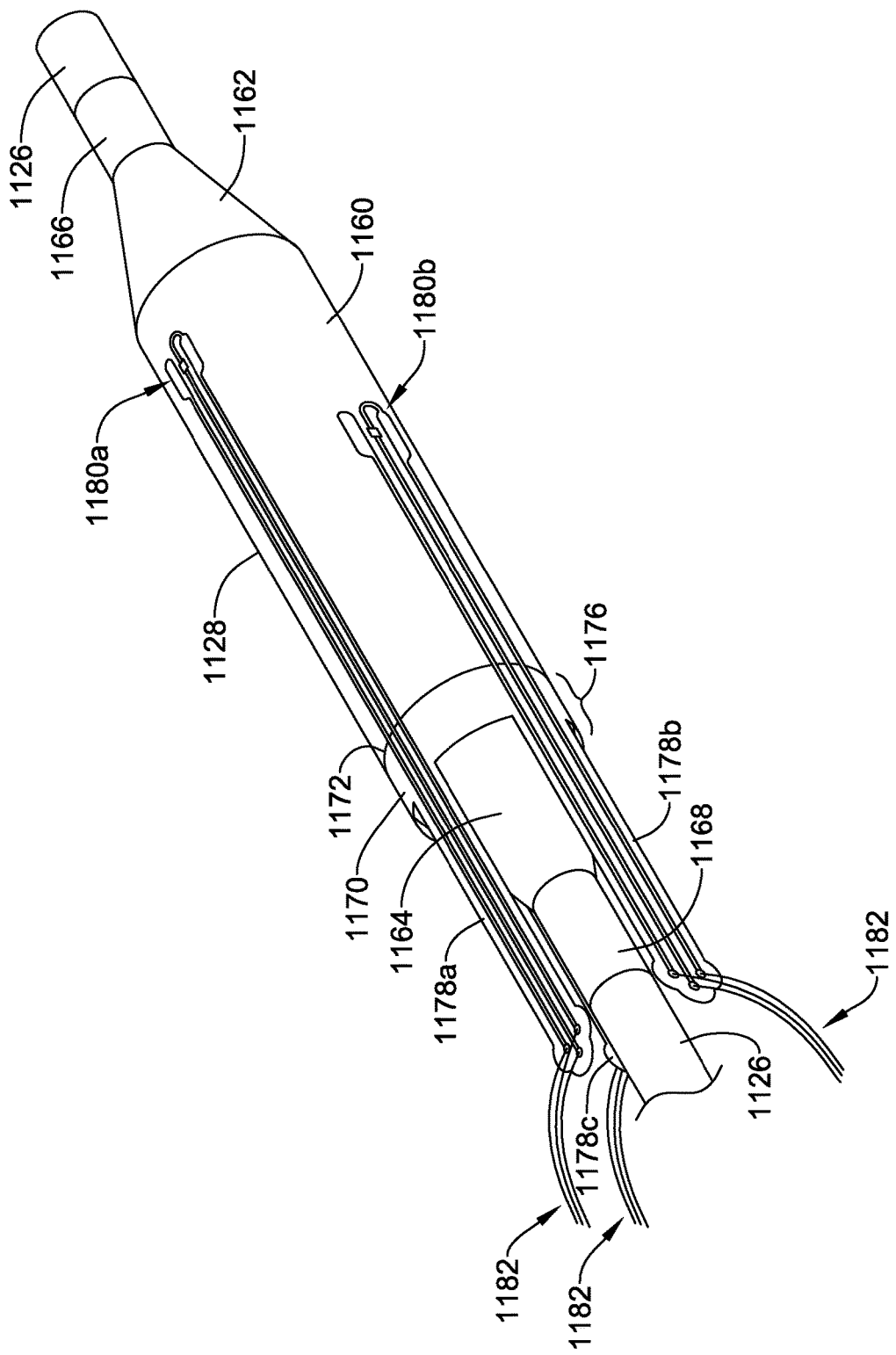
FIGS. 22 and 23 illustrate aspects of manufacturing a portion of an example medical device.

While FIGS. 16-21 illustrate aspects of a method of forming an electrode assembly 1180 on expandable member 1128, it will be appreciated that a similar method may be utilized to form multiple electrode assemblies 1180 on expandable member 1128. For example, FIG. 22 illustrates an expandable member 1128 with a plurality of strips 1178 of a skirt 1170 attached to body region 1160 of expandable member 1128 and extending proximally therefrom. For instance, skirt 1170 may include a plurality of longitudinal strips 1178 of material extending proximally from an annular portion circumferentially surrounding expandable member 1128 and secured to body region 1160 at overlap region 1176. In some embodiments, skirt 1170 shown in FIG. 22, may be resultant of excising excess skirt material, as described above. In other embodiments, skirt 1170 may be a plurality of discrete longitudinal strips of material having a distal end portion secured to expandable member 1128 and extending proximally therefrom at spaced apart locations around the circumference of expandable member 1128 and extend proximally therefrom.

A plurality of electrode assemblies 1180 may be formed directly on outer surface of body region 1160 of expandable member 1128 and directly on outer surface of skirt 1170, such as described above. For example, a first electrode assembly 1180a may be positioned at a first location on body region 1160 of expandable member 1128 and a second electrode assembly 1180b may be positioned at a second location on body region 1160 of expandable member 1128. First electrode assembly 1180a may be offset circumferentially and/or longitudinally relative to second electrode assembly 1180b, for example. Additional electrode assemblies may be positioned on body region 1160 and be offset circumferentially and/or longitudinally relative to first and second electrode assemblies 1180a, 1180b, if desired. For example, a third electrode assembly (on a nonvisible portion of expandable member 1128 of FIG. 22) may be positioned on body region 1160 and be offset circumferentially and/or longitudinally relative to first electrode assembly 1180a and second electrode assembly 1180b.

As described above, conductive members may extend proximally from the electrodes of electrode assemblies 1180 across overlap region 1176 onto skirt 1170. Excess material may be removed from proximal portion of skirt 1170 between the conductive members, to provide a plurality of strips 1178 of material of skirt 1170 having the conductive members applied thereon. FIG. 22 illustrates a first strip 1178a of material of skirt 1170 having conductive members of first electrode assembly 1180a applied directly thereon, a second strip 1178b of material of skirt 1170 having conductive members of second electrode assembly 1180b applied directly thereon, and a third strip 1178c of material of skirt 1170 having conductive members of a third electrode assembly (not shown) applied directly thereon.

Conductive wires 1182 may be electrically connected to conductive members at termination points at a proximal end region of strips 1178 of material of skirt 1170, with the portion of skirt 1170 underlying termination points held longitudinally away from expandable member 1128 and/or radially away from catheter shaft 1126 to avoid inadvertent damage to expandable member 1128 and/or catheter shaft 1126 while making the electrical connections.

Figure 23:
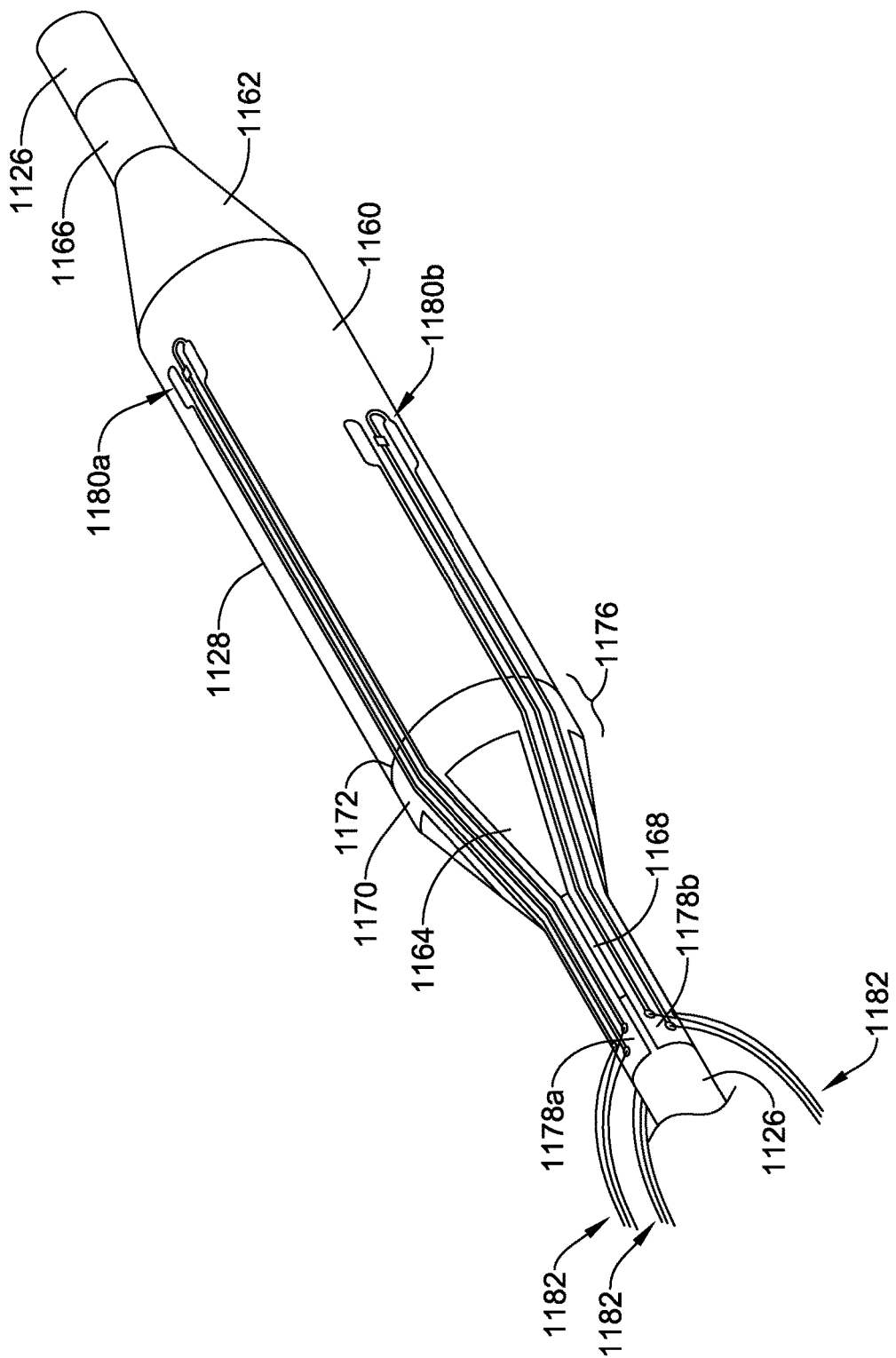

Subsequently, strips 1178 of material of skirt 1170 (e.g., first strip 1178a, second strip 1178b, and third strip 1178c) may be brought into contact with proximal cone region 1164, proximal waist 1168, and/or catheter shaft 1126 to secure strips 1178 thereto. For example, as shown in FIG. 23, proximal portions of strips 1178 having termination points of conductive wires 1182 attached thereon, may be brought into contact with catheter shaft 1126 and/or proximal waist 1168 and attached thereto. For example, strips 1178 of material of skirt 1170 may be adhesively bonded to outer surface of proximal cone region 1164, outer surface of proximal waist 1168 and/or outer surface of catheter shaft 1126, with conductive wires 1182 extending proximally along catheter shaft 1126.

As shown in the figures, strips 1178 of material of skirt 1170, which may initially extend parallel to body region 1160 of expandable member 1128, may be extended along proximal cone region 1164 at an acute angle to central longitudinal axis of expandable member 1128 and body region 1160, such that portions of strips 1178 are juxtaposed with proximal cone region 1164 and proximal waist 1168 of expandable member 1128. Accordingly, strips 1178 of material of skirt 1170 may be adhesively bonded to outer surface of proximal cone region 1164, outer surface of proximal waist 1168 and/or outer surface of catheter shaft 1126.

Similar to that described above, a non-conductive layer (e.g., an electrically insulating mask) may be placed over conductive members of electrode assemblies 1180 along expandable member 1128 and strips 1178 of material of skirt 1170 to electrically insulate conductive members from one another and body tissue during use while leaving one or more portions of active electrodes and return or ground electrodes of electrode assemblies 1180 uncovered to electrically contact tissue during use.

Figure 24:
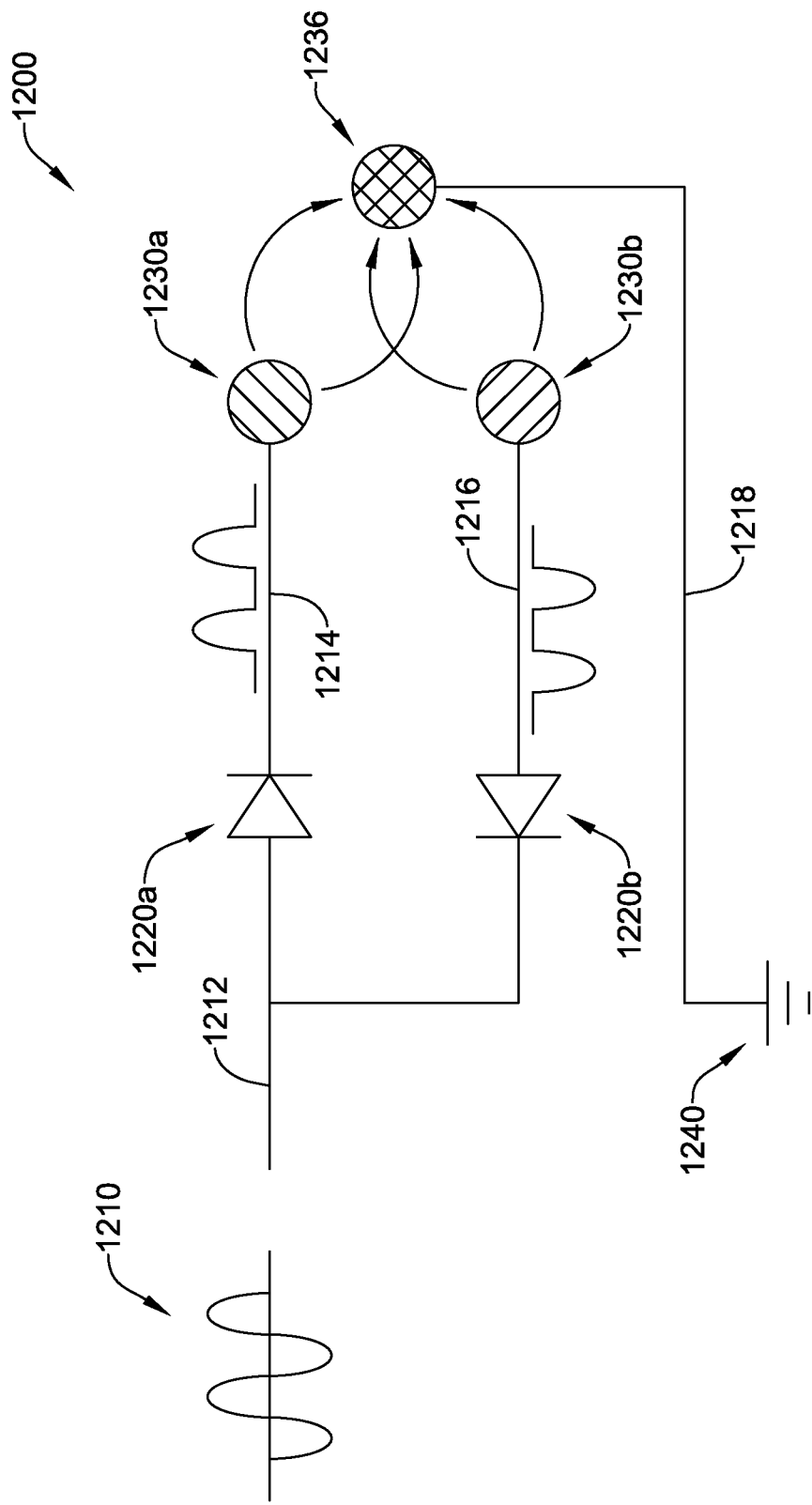
FIG. 24 is a schematic diagram of an exemplary electrical circuit.

FIG. 24 is a schematic diagram of an electrical circuit 1200 which may be used to supply energy to a plurality of active electrodes. Such an electrical circuit 1200 may reduce the number of conductive wires and/or conductive traces used to power an electrode assembly, such as an ablation electrode assembly mounted on an expandable member for use in an ablation procedure, such as a renal nerve ablation procedure. The electrical circuit 1200 may include a first active electrode 1230a, a second active electrode 1230b, and a common ground electrode 1236 capable of being a return electrical pathway for each of the first and second active electrodes 1230a, 1230b. Similar to other embodiments disclosed herein, the first and second active electrodes 1230a, 1230b and common ground electrode 1236 may be mounted on an expandable member (e.g., a balloon) of a catheter with electrical pathways provided to power the electrode assembly. For example, in some instances the first and second active electrodes 1230a, 1230b and common ground electrode 1236, as well as their associated conductive wires/traces, may be included in a flexible circuit formed on or secured to the expandable member (e.g., balloon).

An RF signal 1210, which may be an alternating current, may supply electrical energy to the first and second active electrodes 1230a, 1230b along the signal path 1212. The signal path 1212 may split into a first electrical pathway 1214 supplying electrical energy to the first active electrode 1230a and a second electrical pathway 1216 supplying electrical energy to the second active electrode 1230b. The electrical circuit 1200 may include a first diode 1220a along the electrical pathway 1214 supplying electrical energy to the first active electrode 1230a and a second diode 1220b along the electrical pathway 1216 supplying electrical energy to the second active electrode 1230b. The first diode 1220a may act as a rectifier by allowing only the positive portion of the RF signal 1210 to pass to the first active electrode 1230a and the second diode 1220b may act as a rectifier by allowing only the negative portion of the RF signal 1210 to pass to the second active electrode 1230b. The ground electrode 1236 may be electrically connected to ground 1240 via a return pathway 1218.

In some instances, a DC signal (e.g., either positive or negative) may be added to the RF signal 1210 to shift the amount of energy going to each of the first and second active electrodes 1230a, 1230b. For example, a positive DC signal may be added to the RF signal 1210 to increase the amount of energy going to the first active electrode 1230a, while decreasing the amount of energy going to the second active electrode 1230b. Alternatively a negative DC signal may be added to the RF signal 1210 to decrease the amount of energy going to the first active electrode 1230a while increasing the amount of energy going to the second active electrode 1230b.

Using one or more of the electrical circuits 1200 as illustrated in FIG. 24 to supply electrical energy to a plurality of electrodes of an ablation catheter can reduce the total number of conductive members/wires/traces necessary to supply the electrical energy to the plurality of electrodes. For example, (N) conductive members/wires/traces would be sufficient to serve (2N-1) electrodes using the electrical circuits 1200 as illustrated in FIG. 24. For instance, in an embodiment having six (6) active electrodes and one (1) common ground electrode, a first conductive member/wire/trace may be coupled to the first and second active electrodes, a second conductive member/wire/trace may be coupled to the third and fourth active electrodes, a third conductive member/wire/trace may be coupled to the fifth and sixth active electrodes, and a fourth conductive member/wire/trace may be coupled to the common ground electrode. As another example, in an embodiment having eight (8) active electrodes and one (1) common ground electrode, a first conductive member/wire/trace may be coupled to the first and second active electrodes, a second conductive member/wire/trace may be coupled to the third and fourth active electrodes, a third conductive member/wire/trace may be coupled to the fifth and sixth active electrodes, a fourth conductive member/wire/trace may be coupled to the seventh and eighth active electrodes, and a fifth conductive member/wire/trace may be coupled to the common ground electrode. The following table illustrates some additional configurations.

| Number of conductive members/wires/traces (N) | Number of Electrodes (2N − 1) |
| --- | --- |
| 2 | 3 (2 active; 1 common ground) |
| 3 | 5 (4 active; 1 common ground) |
| 4 | 7 (6 active; 1 common ground) |
| 5 | 9 (8 active; 1 common ground) |
| 6 | 11 (10 active; 1 common ground) |
| 7 | 13 (12 active; 1 common ground) |
| 8 | 15 (14 active; 1 common ground) |

The materials that can be used for the various components of device 12 (and/or other devices disclosed herein) may include those commonly associated with medical devices. For simplicity purposes, the following discussion makes reference to device 12. However, this is not intended to limit the devices and methods described herein, as the discussion may be applied to other similar tubular members and/or components of tubular members or devices disclosed herein.

Device 12 and the various components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or nonsuper-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions device of 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 12 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 12 to achieve the same result.

In some embodiments, a degree of Magnetic Resonance Imaging (MRI) compatibility may be imparted into device 12. For example, portions of device, may be made of a material that does not substantially distort the image and create substantial artifacts (i.e., gaps in the image). Certain ferromagnetic materials, for example, may not be suitable because they may create artifacts in an MRI image. In some of these and in other embodiments, portions of device 12 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Additional Embodiments

A medical device for renal nerve ablation is disclosed. The medical device comprises:
an elongated shaft having a distal region;
an expandable member coupled to the distal region;
one or more active electrodes coupled to the expandable member; and
a common ground electrode coupled to the expandable member, the common ground electrode being capable of being a ground pathway for all of the one or more active electrodes.

Alternatively or additionally to any of the embodiments above, the expandable member includes one or more struts.

Alternatively or additionally to any of the embodiments above, the one or more active electrodes are disposed along the struts.

Alternatively or additionally to any of the embodiments above, the expandable member includes an expandable basket.

Alternatively or additionally to any of the embodiments above, the expandable member includes a balloon.

Alternatively or additionally to any of the embodiments above, a groove is formed along the balloon and wherein at least some of the one or more active electrodes are disposed within the groove.

Alternatively or additionally to any of the embodiments above, a groove is formed along the balloon and wherein the common ground electrode is disposed within the groove.

Alternatively or additionally to any of the embodiments above, a groove is formed along the balloon, wherein at least some of the one or more active electrodes are disposed within the groove and wherein the common ground electrode is disposed within the groove.

Alternatively or additionally to any of the embodiments above, at least one of the one or more active electrodes includes a conductive trace, an electrode region coupled to the conductive trace, and an insulator layer disposed along the conductive trace and the electrode region.

Alternatively or additionally to any of the embodiments above, a flex circuit is disposed along the expandable member and wherein at least some of the one or more active electrodes are disposed along the flex circuit.

Alternatively or additionally to any of the embodiments above, the flex circuit is disposed along a non-conductive region of the expandable member.

Alternatively or additionally to any of the embodiments above, a plurality of active electrodes are disposed along the flex circuit.

Alternatively or additionally to any of the embodiments above, the common ground electrode includes a conductive layer disposed along the expandable member.

Alternatively or additionally to any of the embodiments above, the conductive layer includes gold.

Alternatively or additionally to any of the embodiments above, the common ground electrode includes a lattice disposed along the expandable member.

Alternatively or additionally to any of the embodiments above, the common ground electrode includes a ring-like conductive member disposed about at least some of the one or more active electrodes.

Alternatively or additionally to any of the embodiments above, further comprising a temperature sensor disposed adjacent to at least one of the one or more active electrodes.

Alternatively or additionally to any of the embodiments above, the one or more active electrodes include first and second active electrodes with a first conductive member providing a signal path to both the first and second active electrodes.

Alternatively or additionally to any of the embodiments above, further comprising a first diode along the signal path supplying electrical energy to the first active electrode and a second diode along the signal path supplying electrical energy to the second active electrode.

Alternatively or additionally to any of the embodiments above, the first diode acts as a rectifier by allowing only a positive portion of an RF signal along the signal path to pass to the first active electrode, and the second diode acts as a rectifier by allowing only a negative portion of the RF signal along the signal path to pass to the second active electrode.

A medical device for renal nerve ablation is disclosed. The medical device comprises:
an elongated shaft having a distal region;
an expandable balloon coupled to the distal region;
a plurality of active electrodes coupled to the balloon; and
a common ground electrode coupled to the balloon, the common ground electrode being capable of being a ground pathway for all of the active electrodes.

Alternatively or additionally to any of the embodiments above, a groove is formed along the balloon and wherein at least some of the active electrodes are disposed within the groove.

Alternatively or additionally to any of the embodiments above, the common ground electrode is disposed within the groove.

Alternatively or additionally to any of the embodiments above, at least one of the active electrodes includes a conductive trace, an electrode region coupled to the conductive trace, and an insulator layer disposed along the conductive trace and the electrode region.

Alternatively or additionally to any of the embodiments above, a flex circuit is disposed along the balloon and wherein at least one of the active electrodes is disposed along the flex circuit.

Alternatively or additionally to any of the embodiments above, the flex circuit is disposed along a non-conductive region of the balloon.

Alternatively or additionally to any of the embodiments above, the common ground electrode includes a conductive layer disposed along the balloon.

Alternatively or additionally to any of the embodiments above, the conductive layer includes gold.

Alternatively or additionally to any of the embodiments above, the common ground electrode includes a lattice disposed along the balloon.

Alternatively or additionally to any of the embodiments above, the common ground electrode includes a ring-like conductive member disposed about at least some of the active electrodes.

Alternatively or additionally to any of the embodiments above, further comprising a temperature sensor disposed adjacent to at least one of the active electrodes.

Alternatively or additionally to any of the embodiments above, the common ground electrode covers 50% or more of the outer surface area of the balloon.

Alternatively or additionally to any of the embodiments above, the common ground electrode covers 60% or more of the outer surface area of the balloon.

Alternatively or additionally to any of the embodiments above, the common ground electrode covers 70% or more of the outer surface area of the balloon.

Alternatively or additionally to any of the embodiments above, the common ground electrode covers 80% or more of the outer surface area of the balloon.

Alternatively or additionally to any of the embodiments above, the common ground electrode covers 90% or more of the outer surface area of the balloon.

Alternatively or additionally to any of the embodiments above, further comprising:
a first conductive member providing a signal path to both the first and second active electrodes;
a first diode along the signal path supplying electrical energy to the first active electrode; and
a second diode along the signal path supplying electrical energy to the second active electrode.

Alternatively or additionally to any of the embodiments above, the first diode acts as a rectifier by allowing only a positive portion of an RF signal along the signal path to pass to the first active electrode, and the second diode acts as a rectifier by allowing only a negative portion of the RF signal along the signal path to pass to the second active electrode.

A method for ablating renal nerves is disclosed. The method comprises
advancing a medical device through a blood vessel to a position within a renal artery, the medical device comprising:
an elongated shaft having a distal region,
an expandable member coupled to the distal region,
one or more active electrodes coupled to the expandable member, and
a common ground electrode coupled to the expandable member, the common ground electrode being capable of being a ground pathway for all of the one or more active electrodes;
expanding the expandable member; and
activating at least some of the one or more active electrodes.

A medical device is disclosed. The medical device comprises:
a catheter shaft having a distal region;
a balloon coupled to the distal region;
wherein the balloon includes a first layer of conductive material and a second layer of non-conductive material;
wherein one or more conductive regions are defined along the balloon at regions that are free of the second layer;
a conductive fluid disposed within the balloon;

an active electrode disposed along an outer surface of the balloon; and a return electrode disposed within the balloon.

Alternatively or additionally to any of the embodiments above, the catheter return electrode includes a coil.

A method for manufacturing a medical device is disclosed. The method comprises:

forming a plurality of grooves in an outer surface of a balloon;

disposing an electrode in each of the grooves; and disposing a common return electrode along the outer surface, the common return being positioned adjacent to each of the electrodes.

A medical device for renal nerve ablation is disclosed. The medical device comprises:

an elongated shaft having a distal region;

an expandable balloon coupled to the distal region;

a plurality of active electrodes coupled to the balloon; and a single common ground electrode coupled to the balloon, the single common ground electrode being capable of being a ground pathway for all of the active electrodes.

A method for ablating renal nerves is disclosed. The method comprises:

advancing a medical device through a blood vessel to a position within a renal artery, the medical device comprising:

an elongated shaft having a distal region, an expandable member coupled to the distal region, one or more active electrodes coupled to the expandable member, and a single common ground electrode coupled to the expandable member, the single common ground electrode being capable of being a ground pathway for all of the one or more active electrodes;

expanding the expandable member; and activating at least some of the one or more active electrodes.

A medical device for renal nerve ablation is disclosed. The medical device comprises:

a catheter shaft;

an expandable balloon coupled to the catheter shaft, the balloon having a length, and inner layer, and an outer layer;

wherein the outer layer has a plurality of conductive regions formed therein that extend along the length balloon;

wherein the outer layer has a plurality of non-conductive regions formed therein and disposed adjacent to the conductive region; and an electrode coupled to the conductive region.

Alternatively or additionally to any of the embodiments above, further comprising an electroplated region disposed along at least some of the conductive regions.

A medical device for renal nerve ablation is disclosed. The medical device comprises:

an elongated shaft having a distal region;

an expandable member coupled to the distal region;

one or more active electrodes coupled to the expandable member; and a common ground electrode coupled to the expandable member, the common ground electrode including a conductive member and a plurality of ground pads coupled to the conductive member, the common ground electrode being capable of being a ground pathway for all of the one or more active electrodes.

A medical device for tissue ablation is disclosed. The medical device comprises:

an elongated shaft having a distal region;

an inflatable balloon mounted to the distal region, the inflatable balloon including a body region, a proximal waist secured to the elongated shaft, a distal waist secured to the elongated shaft, a proximal cone region intermediate the proximal waist and the body region, and a distal cone region intermediate the body region and the distal waist;

a skirt attached to the inflatable balloon and extending proximally from the body region; and an electrode assembly applied directly to an outer surface of the body region of the inflatable balloon, the electrode assembly including a first conductive member applied directly to the outer surface of the body region of the inflatable balloon and extending proximally therefrom along an outer surface of the skirt.

Alternatively or additionally to any of the embodiments above, the conductive member is applied directly to the outer surface of the skirt.

Alternatively or additionally to any of the embodiments above, the skirt includes a longitudinal strip of material extending proximally from the body region.

Alternatively or additionally to any of the embodiments above, the skirt includes an annular portion extending circumferentially around the body region of the inflatable balloon.

Alternatively or additionally to any of the embodiments above, the skirt is adhesively bonded to the body region of the inflatable balloon.

Alternatively or additionally to any of the embodiments above, the skirt includes a longitudinal strip of material extending proximally from the body region, the first conductive member applied directly to an outer surface of the longitudinal strip of material, and the electrode assembly includes a second conductive member applied directly to the outer surface of the longitudinal strip of material spaced apart from the first conductive member.

Alternatively or additionally to any of the embodiments above, the electrode assembly includes an active electrode applied directly to the outer surface of the body region of the inflatable balloon and a return electrode applied directly to the outer surface of the body region of the inflatable balloon.

Alternatively or additionally to any of the embodiments above, the first conductive member is in electrical communication with the active electrode and extends proximally therefrom.

Alternatively or additionally to any of the embodiments above, the second conductive member is in electrical communication with the return electrode and extends proximally therefrom.

Alternatively or additionally to any of the embodiments above, further comprising a first electrical wire attached to the first conductive member at a first termination point proximate a proximal end of the first conductive member.

Alternatively or additionally to any of the embodiments above, further comprising a second electrical wire attached to the second conductive member at a second termination point proximate a proximal end of the second conductive member.

Alternatively or additionally to any of the embodiments above, the first and second termination points are located proximal of the proximal waist of the inflatable balloon.

Alternatively or additionally to any of the embodiments above, a distal portion of the skirt is an overlap region secured to the outer surface of the body region of the inflatable balloon.

A medical device for tissue ablation is disclosed. The medical device comprises:

an elongated shaft having a distal region;

an inflatable balloon mounted to the distal region, the inflatable balloon including a body region, a proximal waist secured to the elongated shaft, a distal waist secured to the elongated shaft, a proximal cone region intermediate the proximal waist and the body region, and a distal cone region intermediate the body region and the distal waist;

a skirt having a distal portion attached to an outer surface of the body region of the inflatable balloon and a proximal portion extending proximal of the body region of the inflatable balloon; and an electrode assembly disposed on the body region of the inflatable balloon, the electrode assembly including:

an active electrode applied directly to the outer surface of the body region of the inflatable balloon;

a return electrode applied directly to the outer surface of the body region of the inflatable balloon;

a first conductive member extending proximally from the active electrode, the first conductive member applied directly to the outer surface of the body region of the inflatable balloon and applied directly to an outer surface of the skirt; and a second conductive member extending proximally from the return electrode, the second conductive member applied directly to the outer surface of the body region of the inflatable balloon and applied directly to the outer surface of the skirt.

Alternatively or additionally to any of the embodiments above, the proximal portion of the skirt extends proximal of the proximal waist of the inflatable balloon.

Alternatively or additionally to any of the embodiments above, further comprising:

a first electrical wire attached to the first conductive member at a first termination point proximate a proximal end of the first conductive member; and a second electrical wire attached to the second conductive member at a second termination point proximate a proximal end of the second conductive member.

Alternatively or additionally to any of the embodiments above, the first and second termination points are located proximal of the proximal waist of the inflatable balloon.

Alternatively or additionally to any of the embodiments above, a distal portion of the skirt is an annular portion circumferentially surrounding and overlapping the body region of the inflatable balloon.

Alternatively or additionally to any of the embodiments above, the annular portion of the skirt is adhesively bonded to the body region of the inflatable balloon.

Alternatively or additionally to any of the embodiments above, the skirt includes a strip of material extending proximally from the annular portion of the skirt, the first and second conductive members extending along the strip of material of the skirt.

A method of forming a medical device for tissue ablation is disclosed. The method comprises:

securing a skirt to an inflatable balloon mounted on a catheter shaft, the skirt extending proximal of a body region of the inflatable balloon;

applying an electrode directly to an outer surface of the body region of the inflatable balloon; and applying a conductive member directly to the outer surface of the body region of the inflatable balloon and directly to an outer surface of the skirt, the conductive member extending proximally from the electrode to a proximal end region of the skirt.

Alternatively or additionally to any of the embodiments above, a proximal portion of the skirt is located radially outward away from the catheter shaft and the inflatable balloon while applying the conductive member directly to the outer surface of the skirt.

Alternatively or additionally to any of the embodiments above, the skirt includes an annular member surrounding the body region of the inflatable balloon.

Alternatively or additionally to any of the embodiments above, the annular member is adhered to the body region of the inflatable balloon.

Alternatively or additionally to any of the embodiments above, further comprising:

removing a portion of the skirt while leaving the conductive member extending along a longitudinal strip of the skirt proximal of the body region of the inflatable balloon.

Alternatively or additionally to any of the embodiments above, further comprising:

securing the longitudinal strip with the conductive member thereon to an outer surface of the catheter shaft.

Alternatively or additionally to any of the embodiments above, further comprising:

attaching a conductive wire to a proximal end region of the conductive member at a termination point on the skirt.

Alternatively or additionally to any of the embodiments above, the conductive wire is attached at the termination point while maintaining a portion of the skirt underlying the termination point radially outward away from the catheter shaft.

Alternatively or additionally to any of the embodiments above, further comprising:

removing a portion of the skirt while leaving the conductive member extending along a longitudinal strip of the skirt proximal of the body region of the inflatable balloon and the conductive wire attached at the termination point.

Alternatively or additionally to any of the embodiments above, further comprising:

securing the longitudinal strip with the conductive member thereon to an outer surface of the catheter shaft.

Alternatively or additionally to any of the embodiments above, applying a conductive member directly to the outer surface of the body region of the inflatable balloon and directly to an outer surface of the skirt includes sputter coating an electrically conductive material onto the outer surface of the body region inflatable balloon and the outer surface of the skirt.

Alternatively or additionally to any of the embodiments above, applying an electrode directly to an outer surface of the body region of the inflatable balloon includes sputter coating an electrically conductive material onto the outer surface of the body region of the inflatable balloon.

Alternatively or additionally to any of the embodiments above, further comprising:

plating an electrically conductive material onto the sputter coated electrically conductive material It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device for tissue modulation, comprising:
an elongated shaft having a distal region;
an inflatable balloon mounted to the distal region, the inflatable balloon including a body region, a proximal waist secured to the elongated shaft, a distal waist secured to the elongated shaft, a proximal cone region intermediate the proximal waist and the body region, and a distal cone region intermediate the body region and the distal waist;

a skirt disposed over an outer surface of the inflatable balloon and attached to the inflatable balloon, the skirt circumferentially surrounding the body region and extending proximally from the body region;

an electrode assembly applied directly to an outer surface of the body region of the inflatable balloon, the electrode assembly including a first conductive member applied directly to the outer surface of the body region of the inflatable balloon and extending proximally therefrom along an outer surface of the skirt; and wherein the skirt includes a longitudinal strip of material extending proximally from the body region, the first conductive member applied directly to the outer surface of the longitudinal strip of material.

2. The medical device of claim 1, wherein the skirt includes a longitudinal strip of material extending proximally from the body region, the first conductive member applied directly to an outer surface of the longitudinal strip of material, and the electrode assembly includes a second conductive member applied directly to the outer surface of the longitudinal strip of material spaced apart from the first conductive member.

3. The medical device of claim 2, wherein the electrode assembly includes an active electrode applied directly to the outer surface of the body region of the inflatable balloon and a return electrode applied directly to the outer surface of the body region of the inflatable balloon.

4. The medical device of claim 3, wherein the first conductive member is in electrical communication with the active electrode and extends proximally therefrom.

5. The medical device of claim 4, wherein the second conductive member is in electrical communication with the return electrode and extends proximally therefrom.

6. The medical device of claim 5, further comprising a first electrical wire attached to the first conductive member at a first termination point proximate a proximal end of the first conductive member.

7. The medical device of claim 6, further comprising a second electrical wire attached to the second conductive member at a second termination point proximate a proximal end of the second conductive member.

8. The medical device of claim 7, wherein the first and second termination points are located proximal of the proximal waist of the inflatable balloon.

9. The medical device of claim 3, wherein the skirt includes an annular portion extending circumferentially around the body region of the inflatable balloon and wherein said longitudinal strip of material extends proximally from the annular portion of the skirt.

10. The medical device of claim 9, wherein the skirt is adhesively bonded to the body region of the inflatable balloon.

11. The medical device of claim 1, wherein a distal portion of the skirt is an overlap region secured to the outer surface of the body region of the inflatable balloon.

* * * * *